United States Patent
Donath

(10) Patent No.: US 7,572,770 B2
(45) Date of Patent: Aug. 11, 2009

(54) USE OF AN INTERLEUKIN 1 RECEPTOR ANTAGONIST AND/OR PYRROLIDINEDITHIOCARBAMATE FOR THE TREATMENT OR PROPHYLAXIS OF TYPE 2 DIABETES

(75) Inventor: Marc Donath, Adliswil (CH)

(73) Assignee: University of Zurich, Zurich (CH)

( * ) Notice: Subject to any disclaimer, the term of this patent is extended or adjusted under 35 U.S.C. 154(b) by 219 days.

(21) Appl. No.: 10/517,450

(22) PCT Filed: May 28, 2003

(86) PCT No.: PCT/JP03/06682

§ 371 (c)(1),
(2), (4) Date: Sep. 1, 2005

(87) PCT Pub. No.: WO04/000724

PCT Pub. Date: Dec. 31, 2003

(65) Prior Publication Data

US 2006/0079452 A1 Apr. 13, 2006

Related U.S. Application Data

(60) Provisional application No. 60/392,650, filed on Jun. 27, 2002.

(51) Int. Cl.
*A61K 38/17* (2006.01)
*A61K 31/401* (2006.01)
(52) U.S. Cl. .......................... 514/12; 514/423
(58) Field of Classification Search .................. None
See application file for complete search history.

(56) References Cited

U.S. PATENT DOCUMENTS

| 6,159,460 | A  | * | 12/2000 | Thompson et al. | 424/85.1 |
| 6,294,170 | B1 | * | 9/2001  | Boone et al.    | 424/134.1 |
| 2001/0053764 | A1 |   | 12/2001 | Sims et al. | |

FOREIGN PATENT DOCUMENTS

| EP | 1 018 514 A  | 7/2000 |
| EP | 1018514 A1   | 7/2000 |

OTHER PUBLICATIONS

Giannoukakis et a., Adenoviral gene transfer of the interleukin-1 receptor antagonist protein to human islets prevents IL-1beta-induced beta-cell impairment and activation of islet cell apoptosis in vitro, 1999, Diabetes, vol. 48, pp. 1730-1736.*

Welsh et al., Is there a role for locally produced interlukin-1 in the deleterious effects of high glucose or the type 2 diabetes milieu to human pancreatic islets?, 2005, Diabetes, vol. 54, pp. 3238-3244.*

Donath et al., Mechanisms of beta-cell death in Type 2 diabetes, 2005, Diabetes, vol. 54, Supplement 2, pp. S108-S113.*

Dinarello et al., "Blocking IL-1: interleukin 1 receptor antagonist in vivo and in vitro", Immunology Today, vol. 12, No. 11, 1991, pp. 404-410.

Mandrup-Poulsen et al., "Involvement of interleuken 1 and interleuken 1 antagonist in pancreatic and beta-cell destruction in insulin-dependent diabetes mellitus", Cytokine, vol. 5, No. 3, 1993, pp. 185-191.

Meier et al., "IL-1 receptor antagonist serum levels are increased in human obesity: a possible link to the resistance to leptin?", Journal of Clinical Endocrinology & Metabolism, vol. 87, No. 3, 2002, pp. 1184-1188.

Donath et al., "Hyperglycemia-induced beta-cell apoptosis in pancreatic islets of Psammornys obesus during development of diabetes", Diabetes, vol. 48, No. 4, 1999, pp. 738-744.

Bedoya et al., "Pyrrolidine dithiocarbamate prevents IL-1-induced nitric oxide synthase MRNA, but not superoxide dismutase MRNA, in insulin producing cells", Biochemical and Biophysical Research Communications, Academic Press Inc., Florida, vol. 210, No. 3, 1995, pp. 816-822.

Yamamoto et al., "Role of the NF-kappaB pathway in the pathogenesis of human disease states", Current Molecular Medicine, Bentham Science Publishers, Great Britain, vol. 1, No. 3, 2001, pp. 287-296.

Flodstroem et al., "Cytokines activate the nuclear factor KAPPAB (NF-KAPPAB) and inducenitric oxide production in human pancreatic islets", FEBS Letters, Elsevier Science Publishers, The Netherlands, vol. 385, No. 1/2, 1996, pp. 4-6.

Maedler et al., "Glucose-induced beta cell production of IL-1beta contributes to glucotoxicity in human pancreatic islets", Journal of Clinical Investigation, vol. 110, No. 6, 2002, pp. 851-860.

Blocking IL-1: Interleukin 1 receptor antagonist in vivo and in vitro, Charles A. Dinarello, et al., *Immunology Today*, vol. 12 No. 11 199, pp. 404-410.

Involvement of Interleukin 1 and Interleukin 1 Antagonist in Pancreatic B-Cell Destruction in Insulin-Dependent Diabetes Mellitus, Thomas Mandrup-Poulson, et al., *Cytokine*, vol. 5, No. 3 (May), 1993 pp. 185-191.

Il-1 Receptor Antagonist Serum Levels Are Increased in Human Obesity: A Possible Link to the Resistance to Leptin?, Christoph A. Meier, et al., *The Journal of Clinical Endocrinology & Metabolism* 87(3):1184-1188.

Hyperglucemia-Induced B-Cell Apoptosis in Pancreatic Islets of Psammomys obesus During Development of Diabetes, Marc Y. Donath, et al., *Diabetes*, vol. 48 Apr. 1999, 738-744.

(Continued)

*Primary Examiner*—Robert Landsman
*Assistant Examiner*—Ian Dang
(74) *Attorney, Agent, or Firm*—Birch, Stewart, Kolasch & Birch, LLP

(57) ABSTRACT

Substances that inhibit the action of the members of the IL-1β/NF-κB pathway can be used for protecting and preserving β-cell mass and function in prediabetic and diabetic type 2 patients. Specifically, the present invention relates to the use of an Interleukin 1 receptor antagonist (IL-1Ra) and/or pyrrolidinedithiocarbamate (PDTC) for the treatment or prophylaxis of type 2 diabetes, as well as a method for the treatment of type 2 diabetes.

12 Claims, 10 Drawing Sheets

OTHER PUBLICATIONS

Pyrrolidine Dithiocarbamate Prevents IL-1-Induced Nitric Oxide Synthase mRNA, but not Superoxide Dismutase mRNA, in Insulin Producing Cells, F.J. Bedoyua, et al., *Biochemical and Biophysical Research Communications*, vol. 210, No. 3 1995, pp. 816-822.

Role of the NF-kB Pathway in the Pathogenesis of Human Disease States, Yumi Yamamoto and Richard Gaynor, *Current Molecular Medicine* 2001, 1, pp. 287-296.

Cyokines Activate the Nuclear Factor kB (NF-kB) and Induce Nitric Oxide Production in Human Pancreatic Islets, Maline Flodström, et al., *Federation of European Biochemical Societies* 285 (1996) 4-6.

Glucose-induced B cell Production of IL-1B contributes to Glucotoxicity in Human Pancreatic Islets, Kathrin Maedler, et al., *The Journal of Clinical Investigation*, Sep. 2002, vol. 110, No. 6, pp. 851-860.

Hyperglycaemia as an Inducer as well as a Consequence of Impaired Islet Cell Function and Insulin Resistance: Implications for the Management of Diabetes, R.H. Under, et al., *Diabetologia*, (1985) 28: 119-121.

Monolayer Culture of Adult Rat Pancreatic Islets on Extracellular Matrix: Modulation of B-Cell Function by Chronic Exposure to High Glucose, Nurit Kaiser, et al., *Endocrinology*, vol. 129, No. 4, pp. 2067-2075.

Chronic Hypergycemia Is Associated with Impaired Glucose Influence on Insulin Secretion, A Study in Normal Rats Using Chronic In Vivo Glucose Infusions, L. J. Leahy, et al., *J. Clinical Invest.*, vol. 77 Mar. 1986, pp. 908-915.

Perspective in Diabetes, Type II Diabetes, Glucose "Non-Sense," and Islet Desensitization, R. Paul Robertson, *Diabetes*, vol. 38, Dec. 1989, pp. 1501-1505.

Glucose Toxicity, Luciano Rossetti, M.D., et al., *Diabetes Care*, vol. 13, No. 6, Jun. 1990, pp. 610-630.

Prolonged Exposure of Human Pacreatic Islets to High Glucose Concentrations in Vitro Impairs the B-Cell Function, Decio L. Elizirik, et al. *J. Clin. Invest.*, vol. 90, Oct. 1992, pp. 1263-1268.

Impaired B-Cell Functions Induced by Chronic Exposure of Cultured Human Pancreatic Islets to High Glucose, Sonya Marchak, et al., *Diabetes*, vol. 48m Jun. 1999, pp. 1230-1236.

Glucose Induces B-Cell Apoptosis Via Upregulation of The Fas Receptor in Human Islets, Kathrin Maedler, et al., *Diabetes*, vol. 50, Aug. 2001, pp. 1683-1690.

High Glucose Causes Apoptosis in Cultured Human Pancreatic Islets of Langerhans, A Potential Role for Regulation of Specific Bcl Family Genes Toward an Apoptotic Cell Death Program, Massimo Federici, et al., *Diabetes*, vol. 50, Jun. 2001, pp. 1290-1301.

Glucose and Tolbutamide Induce Apoptosis in Pancreatic B-Cells, Ioulia B. Efanova, et al., *The Journal of Biological Chemistry*, vol. 273, No. 50, Issue of Dec. 11, pp. 33501-33507.

Distinct Effects of Saturated and Monounsaturated Fatty Acids on B-Cell Turnover and Function, K. Maedler, et al., *Diabetes*, vol. 50, Jan. 2001, pp. 69-76.

Long Term Effects of Aminoguanidine on Insulin Release and Biosynthesis: Evidence That the Formation of Advanced Glycosylation End Products Inhibits B Cell Function, Yuji Tajiri, et al., *Endocrinology*, vol. 138, No. 1, pp. 273-280.

Preservation of Insulin mRNA Levels and Insulin Secreation in HIT Cells by Avoidance of Chronic Exposure to High Glucose Concentrations, R. Paul Robertson, *J. Clin. Invest.*, vol. 90, Aug. 1992, pp. 320-325.

Differentiating Glucose Toxicity From Glucose Desensitization: A New Message From the Insulin Gene, R. Paul Robertson, et al., *Diabetes Center and the Division of Diabetes, University of Minnesota Medical School*, 1994.

The Role of Interleukin-1 in the Pathogenesis of IDDM, T. Mandrup-Poulsen, *Diabetologia* (1996) 39: pp. 1005-1029.

Cytokines Cause Functional and Structural Damage to Isolated Islets of Langerhans, T. Mandrup-Poulsen, et al., *Allergy* 1985, 40, pp. 424-429.

Cytoxicity of Human pI 7 Interleukin-1 for Pancreatic Islets of Langerhans, Klaus Bendtzen, et al., *Science*, vol. 232, pp. 1545-1547.

Interleukin 1 Dose-Dependently Affects the Biosynthesis of (pro) Insulin in Isolated Rat Islets of Langerhans, G.A Spinas, et al., *Diabetologia*, (1987) 30: pp. 474-480.

Affinity-Purified Human Interleukin 1 is Cytotoxic to Isolated Islets of Langerhans, T. Mandrup-Poulsen, *Diabetaologia*,(1987) 29: pp. 63-67.

Low Concentrations of Interleukin—1 Stimulate and High Concentrations Inhibit Insulin Release from Isolated Rat Islets of Langerhans, Giatgen A. Spinas, et al., *ACTA Endocrinologia (Copenh)* (1986), 113: pp. 551-558.

Mouse Islet Cell Lysis Mediated by Interleukin-1-Induced Fas, K. Yamada, et al., *Diabetologia* (1996) 39: pp. 1306-1312.

Interleukin-1B-Induced Formation of EPR-Detectable Iron-Nitrosyl Complexes in Islets of Langerhans, John A. Corbett, et al., *The Journal of Biological Chemistry*, vol. 266, No. 32, pp. 21351-21354.

Adenoviral Gene Transfer of the Interleukin-1 Receptor Antagonist Protein To Human Islets Prevents IL-1B-Induced B-Cell Impairment and Activation of Islet Cell Apoptosis In Vitro, Nich Giannoukakis, et al., *Diabetes*, vol. 48, Sep. 1999, pp. 1730-1736.

Prevention of Beta Cell Dysfunction and Apoptosis Activation in Human Islets by Adenoviral Gene Transfer of the Insulin-Like Growth Factor, N. Giannoukakis, et al, *Gene Therapy* (2000) 7, pp. 2015-2022.

Human Islets of Langerhans Express Fas Ligand and Undergo Apoptosis in Response to Interleukin-1B and Fas Ligation, Anne C. Loweth, et al., *Diabetes*, vol. 47, May 1998, pp. 727-732.

Cytotoxic Effects of of Cytokines on Human Pancreatic Islets Cells in Monolayer Culture, Alexander Rabinovitch, et al., *Journal of Clinical Endocrinology and Metabolism*, vol. 71, No. 1, pp. 152-156.

Nitric Oxide Primes Pancreatic B Cells for Fas-Mediated Destruction in Insulin-Dependant Diabetes Mellitus, Giorgio Stassi, et al., *J. Exp. Med.*, vol. 186, No. 8, Oct. 20, 1997, pp. 1193-1200.

Interleukin-1B-Induced Nitric Oxide Synthase Expression by Rat Pancreatic B-Cells: Evidence for the Involvement of Nuclear Factor kB in the Signaling Mechanism, Guim Kwon, et al., *Endocrinology*, vol. 136, No. 11, pp. 4790-4795.

Cytokine Induction of Fas Gene Expression in Insulin-Producing Cells Requires the Transcription Factors NF-kB and C/EBP, Martine I. Darville, et al., *Diabetes*, vol. 50, pp. 1741-1748.

Cytokines Activate the Nuclear Factor kB (NF-kB) and Induce Nitric Oxide Production in Human Pancreatic Islets, Malin Flodström, et al., *Federation of European Biochemical Societies*, 385, (1996) pp. 4-6.

Improved Human Islet Isolation Using a New Enzyme Blend, Liberase, Elina Linetsky, et al., *Diabetes*, vol. 46, Jul. 1997, pp. 1120-1123.

Human Islet Transplantation, José Oberholzer, et al., *Transplantation*, vol. 69, No. 6, Mar. 27, 2000, pp. 1115-1123.

Automated Method for Isolation of Human Pancreatic Islets, Camillo Ricordi, et al., *Diabetes*, vol. 37, Apr. 1988, pp. 413-420.

Monolayer Culture of Adult Rat Pancreatic Islets on Extracellular Matrix: Modulation of B-Cell Function by Chronic Exposure to High Glucose, Nurit Kaiser, et al., *Endocrinology*, vol. 129, No. 4, pp. 2067-2076.

Apoptosis-Inducing Membrane Vesicles, Satoshi Jodo, et al., *The Journal of Biological Chemistry*, vol. 276, No. 43, Issue of Oct. 26, 2001, pp. 39938-39944.

Nitric Oxide Synthase Is Not a Constituent of the Antimicrobial Armature of Human Mononuclear Phagocytes, Markus Schneemann, et al., *The Journal of Infectious Diseases*, 1993, 167, pp. 1358-1363.

Identification of Programmed Cell Death In Situ via Specific Labeling of Nuclear DNA Fragmentation, Yael Gavrieli, et al., *The Journal of Cell Biology*, vol. 119, No. 3, Nov. 1992 pp. 493-501.

N-Terminal DNA-Binding Domains Contribute to Differential DNA-Binding Specificities of NF-kB p50 and p65, Michel B. Toledano, et al., *Molecular and Cellular Biology*, Feb. 1993, vol. 13, No. 2, pp. 852-860.

How NF-kB is Activated: The Role of the IkB Kinase (IKK) Complex, Michael Karin, *Oncogene*, (1999) 18; pp. 6867-6874.

B-Cell Death During Progression to Diabetes, Diane Mathis, et al., *Nature*, vol. 414, Dec. 2001 pp. 792-798.

Evidence of Islet Cell Autoimmunity in Elderly Patients with Type 2 Diabetes, Massimo Pietro, et al., *Diabetes*, vol. 49, Jan. 2000, pp. 32-38.

Antibodies to Glutamic Acid Decarboxylase Discriminate Major Types of Diabetes Mellitus, Merrill J. Rowley, et al., *Diabetes*, vol. 41, Apr. 1992, pp. 548-551.

The Accelerator Hypothesis: Weight Gain as the Missing Link Between Type I and Type II Diabetes, T. J. Wilkin, *Diabetologia* (2001) 44:pp. 914-922.

Processing of Engulfed Apoptotic Bodies Yields T Cell Epitopes, Matteo Bellone, et al., *The Journal of Immunology* 1997, 159:pp. 5391-5399.

Perspectives in Diabetes Neonatal B-Cell Apoptosis, A Trigger for Autoimmune Diabetes?, Jacqueline D. Trudeau, et al., *Diabetes*, vol. 49, Jan. 2000 pp. 1-7.

Activation of Intraislet Lymphoid Cells Causes Destruction of Islet Cells, Paul E. Lacy, et al., *American Journal of Pathology*, vol. 138, No. 5, May 1991, pp. 1183-1190.

The Intraislet Macrophage and Type I Diabetes, Paul E. Lacy M.D., *The Mount Sinai Journal of Medicine*, vol. 61, No. 2, Mar. 1994, pp. 170-174.

Potential Role of Resident Islet Macrophage Activation in the Initiation of Autoimmune Diabetes, Marc Arnush, et al., *The Journal of Immunology*, 1998, 160: pp. 2684-2691.

Pancreatic B-Cell Damage Mediated by B-Cell Production of Interleukin-1, Monique R. Heitmeier, et al., *The Journal of Biological Chemistry*, vol. 276, No. 14, Apr. 6, 2001, pp. 11151-11158.

Hyperproinsulinemia and Insulin Deficiency in the Diabetic *Psammomys obesus* M. Gadot, et al., *Endocrinology*, May 20, 2005, vol. 135, No. 2.

Monocyte Chemoattractant Protein-1 is Expressed in Pancreatic Islets from Prediabetic NOD Mice and In INterleukin-1B-exposed Human and Rat Islet Cells, M.-C Chen, et al., Diabetologia (2001) 44: pp. 325-332.

B-Cell Apoptosis and Defense Mechanisms, Lessons from Type 1 Diabetes, Decio L. Elizirik, et al., *Diabetes*, vol. 50, Supp. 1, Feb. 2001, pp. S64-S69.

Cytokines Induce Apoptosis in B-Cells Isolated From Mice Lacking the Inducible Isoform of Nitric Oxide Synthase (iNOS-/-), Dongbo Liu, et al., *Diabetes*, vol. 49, Jul. 2000, pp. 1116-2000.

Nitric Oxide Production and Fas Surface Expression Mediate Two Independent Pathways of Cytokine-Induced Murine B-Cell Damage, Urs Zumsteg, et al., *Diabetes*, vol. 49, Jan. 2000, pp. 39-47.

Protection of Human Islets from the Effects of Interleukin-1B by Adenoviral Gene Transfer of an IkB Repressor, Nich Giannoukakis, et al., *The Journal of Biological Chemistry*, vol. 275, No. 47, Issue of Nov. 24, 2000, pp. 36509-36513.

Nitric Oxide Mediates Cytokine-Induced Inhibition of Insulin Secretion by Human Islets of Lanerhans, John A. Corbett, et al., *Proc. Natl. Acad. Sci. USA*, vol. 90 pp. 1731-1735, Mar. 1993 *Medical Sciences*.

Hyperglycemia-Induced Activation of Nuclear Transcription Factor kB in Vascular Smooth Muscle Cells, Kiran Kumar, et al., *Diabetes*, vol. 48, Apr. 1999, pp. 855-864.

Inhibition of Cytokine-Induced NF-kB Activation by Adenovirus-Mediated Expression of a NF-kB Super-Repressor Prevents B-Cell Apoptosis, Harry Heimberg, et al., *Diabetes*, vol. 50, Oct. 2001, pp. 2219-2224.

Imidazoline Compounds Protect Against Interleukin 1B-Induced B-Cell Apoptosis, Sergei V. Zaitsev, et al., *Diabetes*, vol. 50, Suppl. 1, Feb. 2001, pp. S70-S76.

Improved Beta-Cell Function after Intensive Insulin Treatment in Severe Non-Insulin-Dependent Diabetes, Benjamin Glaser, et al., *ACTA Endocrinologica*, (*Copenh*) 1988, 118: pp. 365-373.

B-Cell Deficit and Increased B-Cell Apoptosis in Humans With Type 2 Diabetes, Alexandra E. Butler, et al., *Diabetes*, vol. 52, Jan. 2003, pp. 102-110.

Early Differential Defects of Insulin Secretion and Action in 19-Year-Old Caucasian Men Who Had Low Birth Weight, Christine B. Jensen, et al., *Diabetes*, vol. 51, Apr. 2002, pp. 1271-1280.

Age-Dependent Impact of Zygosity and Birth Weight on Insulin Secretion and Insulin Action in Twins, P. Poulsen, et al., *Diabetologia* (2002), pp. 1649-1657.

Metabolic Impact of a Family History of Type 2 Diabetes. Results from a European Multicentre Study (EGIR), A. Vaag, et al., *2001 Diabetes UK. Diabetic Medicine*, 18, pp. 553-540.

Journal Symposium, Islet Growth and Development in the Adult, S. Bonner-Weir, *Journal of Molecular Endocrinology* (2002) 24, pp. 297-302.

Islet Pathology and the Pathogenesis of Type 1 and Type 2 Diabetes Mellitus Revisited, Günter Klöppel, et al., *Surv. Synth. Path. Res.* 4: pp. 110-125 (1985).

Reduced Beta-Cell Mass and Expression of Oxidative Stress-Related DNA Damage in the Islet of Japanese Type II Diabetic Patients, H. Sakuraba, et al., *Diabetologia* (2002) 45: pp. 85-96.

Selective B-Cell Loss and z-Cell Expansion in Patients with Type 23 Diabetes Mellitus in Korea, Kun Ho Yoon, et al., *The Journal of Clinical Endocrinology & Metabolism* 88(5), pp. 2300-2308.

B-Cell Dysfunction and Insulin Resistance in Type 2 Diabetes: Role of Metabolic and Genetic Abnormalities, Derek LeRoith, M.D., Ph.D., FACP, *The American Journal of Medicine*, vol. 113(6A), pp. 3S-11S.

Fatty Acids, Lipotoxicity and Insulin Secretion, J.D. McGarry, et al., *Diabetologia* (1999) 42: pp. 128-138.

The Glucose Fatty Acid Cycle in Obesity and Maturity Onset Diabetes Mellitus, P. J. Randle, et al., *Annals New York Academy of Sciences*, pp. 324-333.

Lipotoxicity in the Pathogenesis of Obesity-Dependent NIDDM, Genetic and Clinical Implications, Roger H. Unger, *Diabetes*, vol. 44, Aug. 1995, pp. 863-870.

Monounsaturated Fatty Acids Prevent the Deleterious Effects of Palmitate and High Glucose on Human Pancreatic B-Cell Turnover and Function, Kathrin Maedler, et al., *Diabetes*, vol. 52, Mar. 2003, pp. 726-733.

Glucose-Induced B Cell Production of IL-1B Contributes to Glucotoxicity in Human Pacreatic Islets, Kethrin Maedler, et al., *The Journal of Clinical Investigation*, Sep. 2002, vol. 110, No. 6, pp. 851-860.

FLIP Switches FAS-Mediated Glucose Signaling in Human Pancreatic B Cells From Apoptosis to Cell Replication, Kathrin Maedler, et al., *PNAS*, Jun. 11, 2002, vol. 99, No. 12, pp. 8236-8241.

Islet Secretion in a New Experimental Model for Non-Insulin-Dependent Diabetes, G. C. Weir, et al., *Diabetes*, vol. 30, Jul. 1981, pp. 590-595.

Partial Pancreatectomy in the Rat and Subsequent Defect in Glucose-Induced Insulin Release, S. Bonner-Weir, *J. Clin. Invest.*, vol. 71, Jun. 1983, pp. 1544-1554.

Hyperglycaemia as an inducer as well as a Consequence of Impaired Islet Cell Function and Insulin Resistance: Implications for the management of diabetes, R. H. Under, et al., *Diabetologia* (1985) 28: pp. 119-121.

Positional Cloning of the Mouse Obese Gene and its Human Homologue, Yiying Zhang, et al., *Nature*, vol. 372, Dec. 1994, pp. 425-432.

Recombinant Mouse OB Protein: Evidence for a Peripheral Signal Linking Adiposity and Central Neural Networks, L. Arthur Campfield, et al., *Science*, vol. 269, Jul. 28, 1995, pp. 546-549.

Expression of the Functional Leptin Receptor mRNA in Pancreatic Islets, Valur Emilsson, et al., *Diabetes*, vol. 46, Feb. 1997, pp. 313-316.

Leptin Receptors Expressed on Pancreatic B-Cells, T. Kieffer, et al., *Biochemical and Biophysical Research Communications* 224, pp. 522-527 (1996), *Art. 1059*.

Inhibition of Glucose-Induced Insulin Secretion by Long-Term Preexposure of Pancreatic Islets to Leptin, R. Roduit, et al., *FEBS Letters* 415 (1997) pp. 179-182.

Fetal Pancreatic Islets Express Functional Leptin Receptors and Leptin Stimulates Proliferation of Fetal Islet Cells, MS Islam, et al., *International Journal of Obesity* (2000) 24, pp. 1246-1253.

Leptin Increases the Viability of Isolated Rat Pancreatic Islets by Suppressing Apoptosis, S. Okuya, et al., *Endocrinology*, 142, (11) 4827-4830.

Protection Against Lipoapoptosis of B Cells Through Leptin-Dependent Maintenance of Bcl-2 Expression, M. Shimabukuro, et al., Proc. Natl. Acad. Sci. USA, vol. 95, pp. 9558-9561.

Leptin Induces Proliferation of Pancreatic B Cell Line MIN6 through Activation of Mitogen-Activated Protein Kinase, K. Tanabe, et al., *Biochemical and Biophysical Research Communications*, 241: pp. 765-768(1997).

A Urine Inhibitor of Inerleukin 1 Activity Affects Both Interleukin 1a and 1b But Not Tumor Necrosis Factor, P. Seckinger, et al., *The Journal of Immunology*, vol. 139, 1541-1545, No. 5, Sep. 1, 1987.

A Urine Inhibitor of Interleukin 1 Activity That Blocks Ligand Binding, P. Seckinger, et al., *The Journal of Immunology*, vol. 139, 1546-1549.

Biological Role of Interleukin 1 Receptor Antagonist Isoforms, W. Arend, et al., *Am Rheum Dis* 2000:59(suppl 1) i60-i64.

Leptin Directly Induces the Secretion of Interleukin 1 Receptor Antagonist in Human Monocytes, C. Gabay, et al., *The Journal of Clinical Endocrinology and Metabolism*, vol. 86, No. 2, pp. 783-791.

Inflammatory Mediators and Islet B-Cell Failure: A Link Between Type 1 and Type @ Diabetes, M. Donath, et al., *J. Mol. Med*, (2003) 81: 455-470.

Non-Insulin Dependent Diabetes Mellitus . . . , K. Polonsky M.D., et al., *Seminars in Medicine of the Beth Israel Hospital*, Boston, vol. 334, No. 12, pp. 777-783.

\* cited by examiner

USE OF AN INTERLEUKIN 1 RECEPTOR ANTAGONIST AND/OR PYRROLIDINEDITHIOCARBAMATE FOR THE TREATMENT OR PROPHYLAXIS OF TYPE 2 DIABETES

FIELD OF THE INVENTION

The present invention relates to the use of an Interleukin 1 receptor antagonist (IL-1Ra) and/or pyrrolidinedithiocarbamate (PDTC) for the treatment or prophylaxis of type 2 diabetes, as well as a method for the treatment of type 2 diabetes.

BACKGROUND OF THE INVENTION

Type 2 diabetes mellitus results from an inadequate adaptation of the functional pancreatic β-cell mass in the face of insulin resistance. In turn, hyperglycemia per se has secondary adverse effects on β-cells. Indeed, several studies have shown that chronic elevation of blood glucose concentration impairs β-cell function, leading to the concept of "glucotoxicity" (1-7). Moreover, elevated glucose concentrations induce β-cell apoptosis in cultured islets from diabetes-prone *Psammomys obesus* (8), from human islets (9;10) and at higher concentrations in rodent islets (8;11;12). Various molecular mechanisms have been proposed to underlie glucose-induced β-cell dysfunction, including formation of advanced glycation end products (13), direct impairment of insulin gene transcription and proinsulin biosynthesis (14;15) and reduced binding activity of pancreatic duodenal homeobox 1 (PDX-1) (7). Recently, the present inventor and co-workers proposed a mechanism underlying glucose-induced β-cell apoptosis in human islets, which involves up-regulation of Fas receptors by elevated glucose levels (9). However, the mediator of glucose-induced Fas-expression and its role in glucotoxicity remains unknown.

Interleukin 1 receptor antagonist (IL-1Ra) is a mature glycoprotein of 152 amino acid (aa) residues. The protein has a native molecular weight of 25 kDa, and the molecule shows limited aa sequence homology to IL-1α (19%) and IL-1β (26%).

The effects produced by IL-1α and IL-1β result from the binding of these factors to two distinct cell surface receptors, IL-1R types I and II. Recent results suggest that only the type I receptor is capable of transducing a signal and producing a biological effect. The inhibitory action of IL-1Ra results from its binding to the type I IL-1R. Although this binding is of high-affinity (Kd=200 pM), it does not result in receptor activation (signal transduction), an effect attributed to the presence of only one receptor binding motif on IL-1Ra vs. two such motifs on IL-1α and IL-1β. Since the affinity of IL-1Ra for the type I receptor is comparable to that for IL-1α and IL-1β, down-regulation of IL-1 activity seems to be due to competitive inhibition. Notably, IL-1Ra also binds to the non-signal transducing type II IL-1R (Kd=7 nM), but with considerably lower affinity than that shown by IL-1β (Kd=0.3-2.0 nM). This makes sense teleologically in that two mechanisms designed to inhibit the actions of IL-1β (i.e., IL-1Ra binding to IL-1R type I and IL-1β binding to IL-1R type II) should not compete with each other.

It has been proposed to use IL-1β for mediating both impaired function and destruction of pancreatic β-cell during the development of autoimmune type 1 diabetes (16). In keeping with this, treatment of rodent islets with IL-1β results in a potent inhibition of insulin secretion followed by islet destruction (17-23). In human islets, IL-1β has further been shown to impair insulin release and to induce Fas expression enabling Fas-triggered apoptosis (9;24-28). Finally, activation of the nuclear transcription factor NF-κB is required for IL-1β-induced Fas expression (29-31). Part of these IL-1β effects are reminiscent of the toxic effects of elevated glucose concentrations.

Zaitsev et al. (60) propose the treatment of type 2 diabetes with imidazoline compounds.

SUMMARY OF THE INVENTION

The inventor and co-workers believe that glucose may induce IL-1β secretion from β-cells in the absence of an autoimmune process. The present inventor and co-workers has identified β-cells as the cellular source of glucose-induced IL-1β in cultured human islets, and has confirmed this using tissue sections from the pancreas of type 2 diabetic patients and of *Psammomys obesus*. The role of such endogenously produced IL-1β in β-cell glucotoxicity has also been explored.

In type 2 diabetes, chronic hyperglycemia is suggested to be detrimental to pancreatic β-cells, causing impaired insulin secretion. Interleukin-1β (IL-1β) is a pro-inflammatory cytokine acting during the autoimmune process of type 1 diabetes. IL-1β inhibits β-cell function and promotes Fas-triggered apoptosis in part by activating the transcription factor NF-κB. Recently, the present inventor and co-workers have shown that increased glucose concentrations also induce Fas-expression and p-cell apoptosis in human islets. The aim of the present study was to test the hypothesis that IL-1β may mediate the deleterious effects of high glucose on human β-cells. In vitro exposure of islets from nondiabetic organ donors to high glucose levels resulted in increased production and release of IL-1β, followed by NF-κB activation, Fas up-regulation, DNA-fragmentation and impaired β-cell function. The interleukin-1 receptor antagonist IL-1Ra protected cultured human islets from these deleterious effects. β-cells themselves were identified as the islet cellular source of glucose-induced IL-1β. In vivo, IL-1β producing p-cells were observed in pancreatic sections of type 2 diabetic patients but not in nondiabetic control subjects. Similarly, IL-1β was induced in β-cells of the gerbil *Psammomys obesus* during development of diabetes. Treatment of the animals with phlorizin normalized plasma glucose and prevented β-cell expression of IL-1β. These findings implicate an inflammatory process in the pathogenesis of glucotoxicity in type 2 diabetes and identify the IL-1β/NF-κB pathway as a target to preserve β-cell mass and function in this condition.

Thus, the present inventor has found that Interleukin 1 receptor antagonist (IL-1Ra) and/or the NF-κB inhibitor pyrrolidinedithiocarbamate (PDTC) can be useful for the treatment or prophylaxis of type 2 diabetes.

One aspect of the invention relates to the use of an Interleukin 1 receptor antagonist (IL-1Ra) for the preparation of a medicament for the treatment or prophylaxis of type 2 diabetes in a mammal.

Another aspect of the invention relates to the use of pyrrolidinedithiocarbamate (PDTC) for the preparation of a medicament for the treatment or prophylaxis of type 2 diabetes in a mammal.

A third aspect of the invention relates to the combined use of an Interleukin 1 receptor antagonist (IL-1Ra) and pyrrolidinedithiocarbamate (PDTC) for the preparation of a medicament for the treatment or prophylaxis of type 2 diabetes in a mammal.

A fourth aspect of the invention relates to the method of treating or prophylactically suppressing type 2 diabetes, wherein the method comprises administering to a mammal in need thereof a sufficient amount of an Interleukin 1 receptor antagonist (IL-1Ra).

A fifth aspect of the invention relates to the method of treating or prophylactically suppressing type 2 diabetes, wherein the method comprises administering to a mammal in need thereof a sufficient amount of pyrrolidinedithiocarbamate (PDTC).

A sixth aspect of the invention relates to the method of treating or prophylactically suppressing type 2 diabetes, wherein the method comprises administering to a mammal in need thereof a sufficient amount of a combination of an Interleukin 1 receptor antagonist (IL-1Ra) and pyrrolidinedithiocarbamate (PDTC).

A, Secretion of IL-1β from human islets cultured on extracellular matrix-coated dishes for 4 days in 5.5, 11.1 or 33.3 mM D-glucose or in 5.5 mM D-glucose plus 27.8 mM L-glucose. Each bar represents the mean of eight experiments±SE from eight separate donors. *, P<0.01 relative to islets at 5.5 mM glucose. B, Secretion of IL-1β from human islets during 44-hour cultured in a suspension at 5.5 or 33.3 mM D-glucose. Data were collected from four tubes per treatment in two separate experiments from two donors. Data are represented as mean±SE. *, P<0.01 relative to islets at 5.5 mM glucose. C, Immunoblotting of pro-IL-1β, IL-1β and actin. Human islets cultured in a suspension at 5.5 or 33.3 mM glucose were analysed after 44 hours of incubation. One experiment out of eleven from eleven donors is shown. In seven experiments, glucose induced IL-1β, in three experiments, IL-1β remained unchanged and in one, it was decreased. D, RT-PCR detection and quantification of IL-1β mRNA expression. Total RNA was isolated from human islets cultured for 44 hours in a medium containing 5.5 or 33.3 mM glucose. In the Light Cycler quantitative PCR system, the level of IL-1β expression was normalized against GAPDH and the results expressed as mRNA levels relative to control incubations at 5.5 mM. Results are shown+/−SE for 6 independent experiments from 6 donors. *, P<0.05 relative to islets at 5.5 mM glucose.

Figure 2:
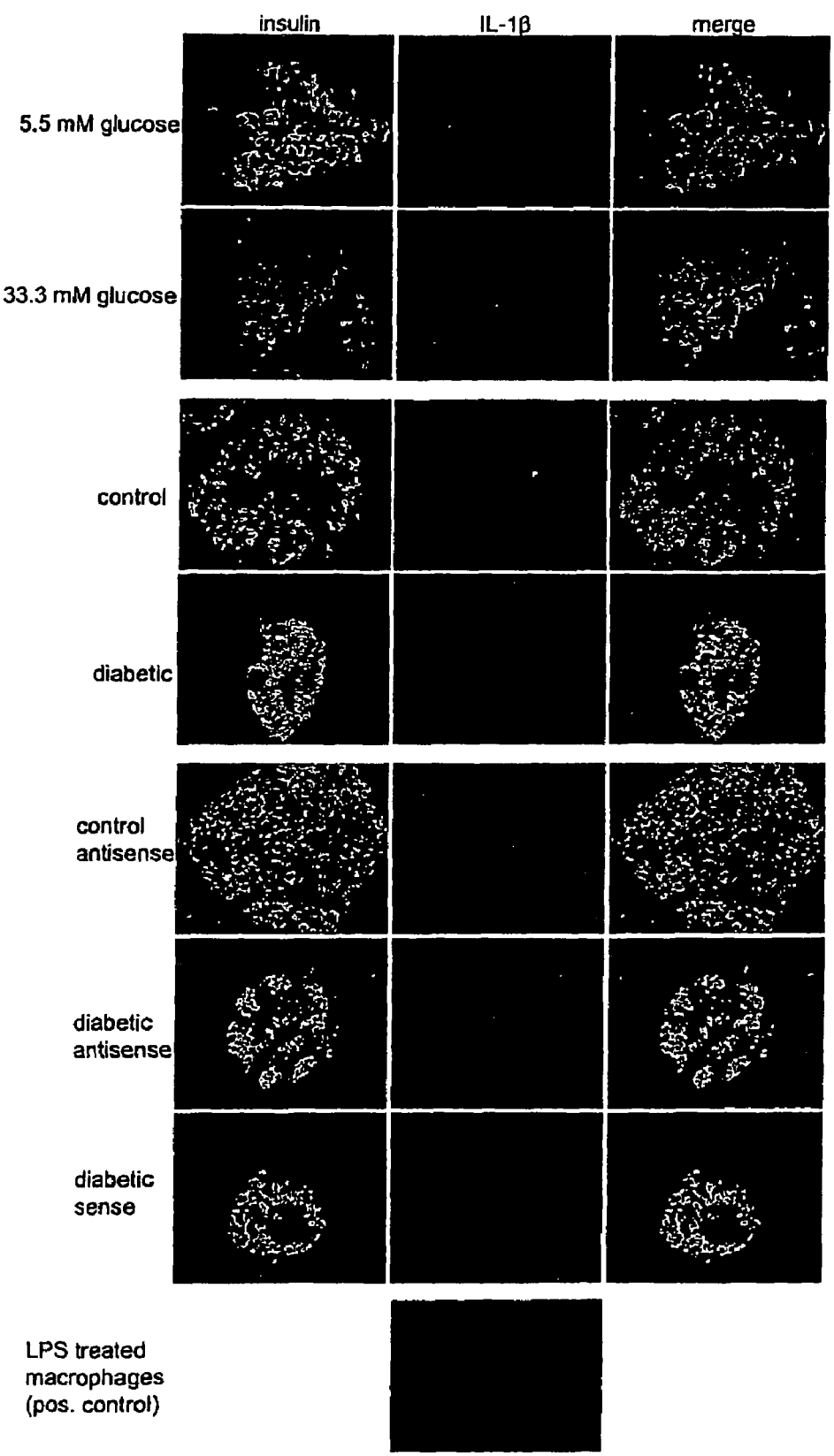

FIG. 2—Expression of IL-1β by human β-cells exposed to a diabetic milieu.

Double immunostaining for IL-1β (B, D) and insulin (A, C) in human islets cultured on extracellular matrix-coated dishes and exposed for 4 days to media containing 5.5 mM glucose (A, B) or 33.3 mM glucose (C, D). Double immunostaining for IL-1β (F, H) and insulin (E, G) in tissue sections of pancreases from a non-diabetic patient (E, F) and from a patient with type 2 diabetes (G, H). In situ hybridization for IL-1β mRNA (J, L, N) double immunostained for insulin (I, K, M) in tissue sections of pancreases from a patient with type 2 diabetes with anti-sense probe (L) and with sense probe (negative control) (N), and from a non-diabetic patient using anti-sense probe (J). Immunostaining for IL-1β in lipopolysaccharide (LPS) treated macrophages (positive control) (O). 250-fold magnification.

Figure 3:
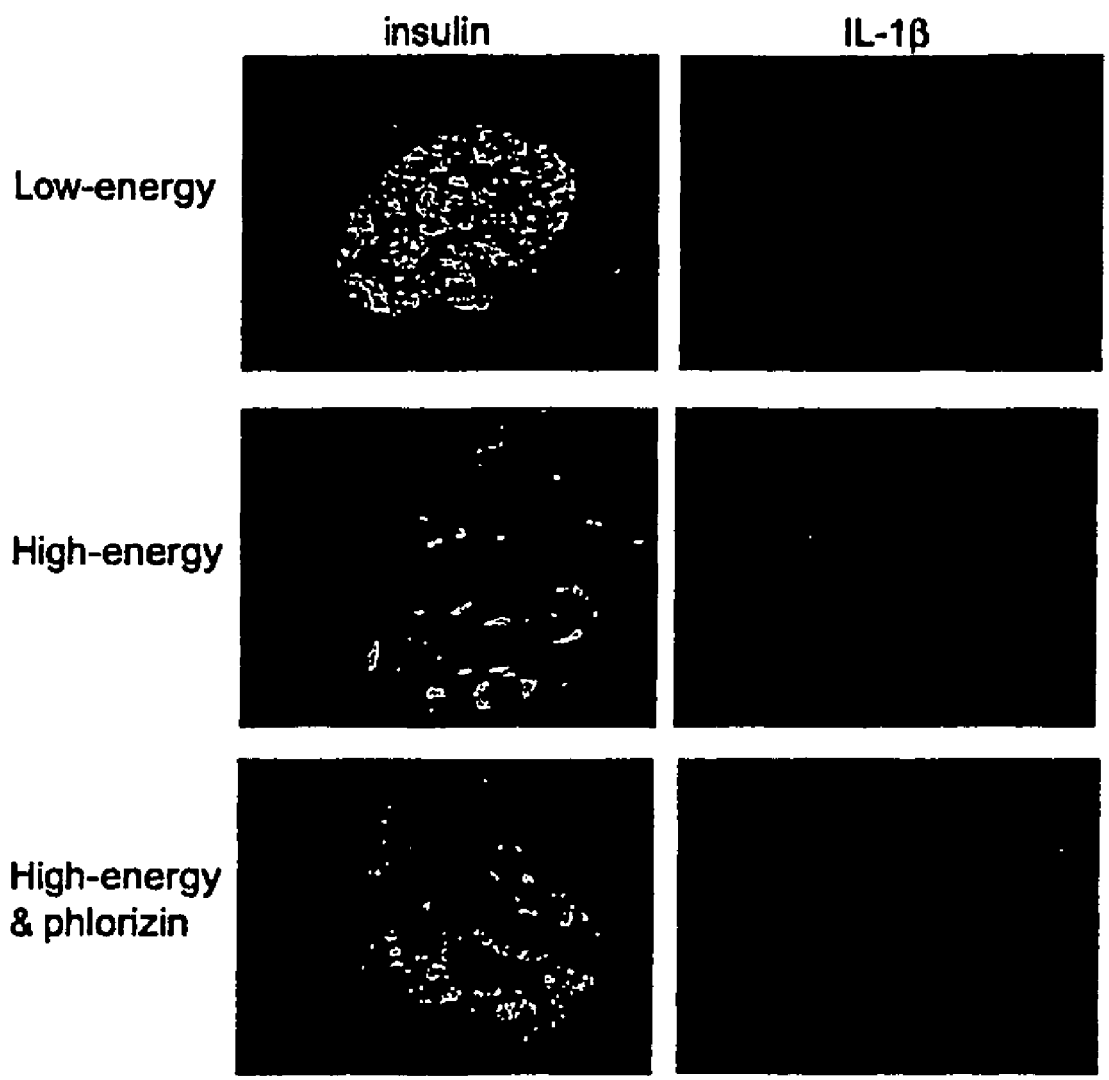

FIG. 3—β-cell expression of IL-1β during development of diabetes in *Psammomys obesus*. Double immunostaining for IL-1β (B, D, F) and insulin (A, C, E) in tissue sections of pancreases from a fasted *Psammomys obesus* on low-energy diet (blood glucose 4 mM) (A, B), from an animal on a high-energy diet for 8 days without (blood glucose 13.6 mM) (C, D) and with injections of the glucopenic drug phlorizin (blood glucose 5.6 mM) (E, F). 250-fold magnification.

Figure 4:
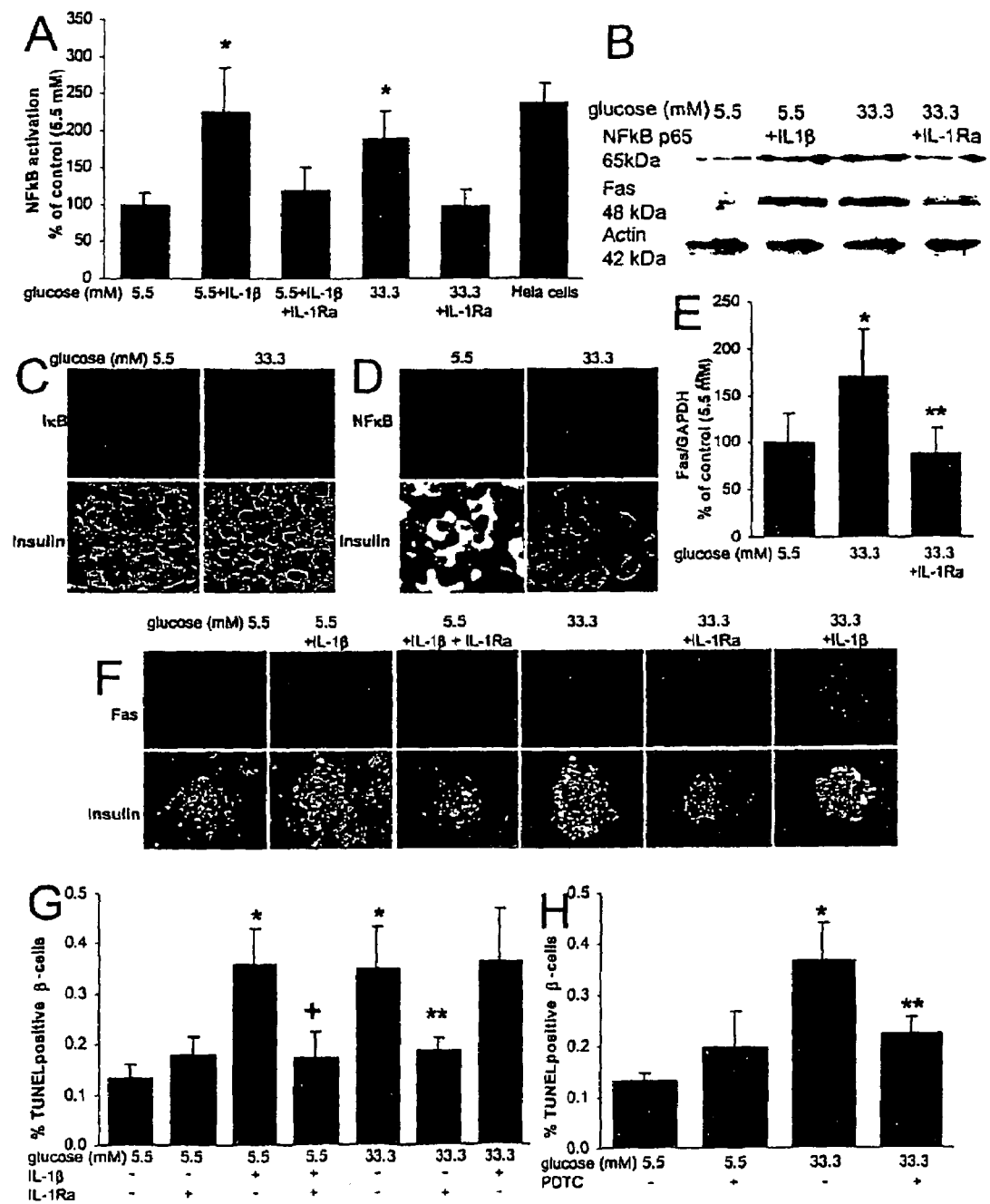

FIG. 4—Glucose decreases β-cell's IκB expression and induces IL-1β-meditated NF-κB activation, Fas expression and DNA fragmentation.

A, Relative NF-κB activity. Human islets were cultured in a suspension for 44 hours in 5.5 or 33.3 mM glucose alone or in the presence of IL-1β, IL-1Ra or both. HeLa cells, stimulated with 5 ng/ml IL-1α, were used as positive control. Each bar represents the mean of three experiments±SE from three separate donors. *, P<0.05 relative to islets at 5.5 mM glucose. B, Immunoblotting of NF-κB (p65), Fas and actin. Human islets cultured in a suspension at 5.5 or 33.3 mM glucose with and without IL-1β or IL-1Ra were analyzed after 44 hours of incubation. The antibodies were blotted on the same membrane after stripping. One out of three experiments from three donors is shown. Each experiment displayed similar results. C, Double immunostaining for IκB (1, 3) and insulin (2, 4) in sections of cultured human islets exposed for 44 hours to media containing 5.5 mM (1, 2) or 33.3 mM glucose (3, 4). D, Double immunostaining for NF-κB (p65) (1, 3) and insulin (2, 4) in human islets exposed for 44 hours to media containing 5.5 mM (1, 2) or 33.3 mM glucose (3, 4). The arrows mark β-cell nuclei stained positive for NF-κB. 750-fold magnification. E, RT-PCR detection and quantification of Fas mRNA expression. Total RNA was isolated from human islets cultured for 44 hours in a medium containing 5.5 or 33.3 mM glucose alone or in the presence of IL-1Ra. In the Light Cycler quantitative PCR system, the level of Fas expression was normalized against GAPDH and the results expressed as relative mRNA levels to control incubations at 5.5 mM. Results are shown+/−SE for 6 independent experiments from 6 donors. *, P<0.05 relative to islets at 5.5 mM glucose; **, P<0.05 relative to islets at 33.3 mM glucose. F, Double immunostaining for Fas (1, 3, 5, 7, 9, 11) and insulin (2, 4, 6, 8, 10, 12) in human islets exposed for 4 days to media containing 5.5 mM glucose without (1, 2) and with IL-1β alone (3, 4) or with IL-1Ra (5, 6) or 33.3 mM glucose without (7, 8) and with IL-1Ra (9, 10) or IL-1β (11, 12). 250-fold magnification. G, Human islets were cultured for 4 days in 5.5 and 33.3 mM glucose alone or in the presence of IL-1β and/or IL-1Ra or (H) with and without PDTC. Results are means±SE of the percent of TUNEL-positive β-cells. The mean number of islets scored from each donor was 49 (range 35-63) for each treatment condition. Islets were isolated from five organ donors. *, P<0.01 relative to islets at 5.5 mM glucose; **, P<0.01 relative to islets at 33.3 mM glucose. +, P<0.01 relative to islets at 5.5 mM glucose plus IL-1β.

Figure 5:
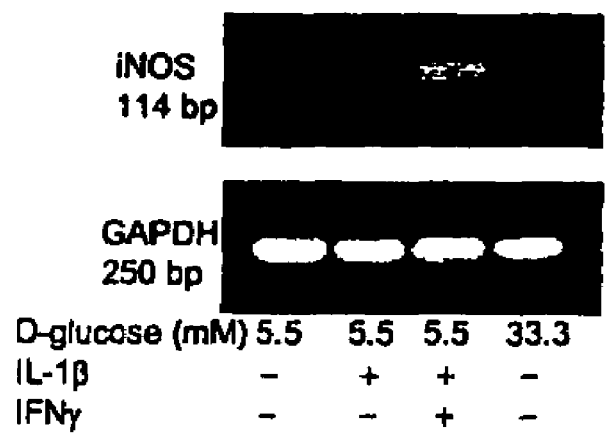

FIG. 5—Failure of glucose and IL-1β to induce iNOS mRNA expression in human islets.

RT-PCR analysis of iNOS expression by islets cultured for 44 hours in 5.5 and 33.3 mM glucose or with IL-1β alone or in combination with IFNγ (positive control). GAPDH was used as control. One out of three experiments from three donors is shown.

Figure 6:
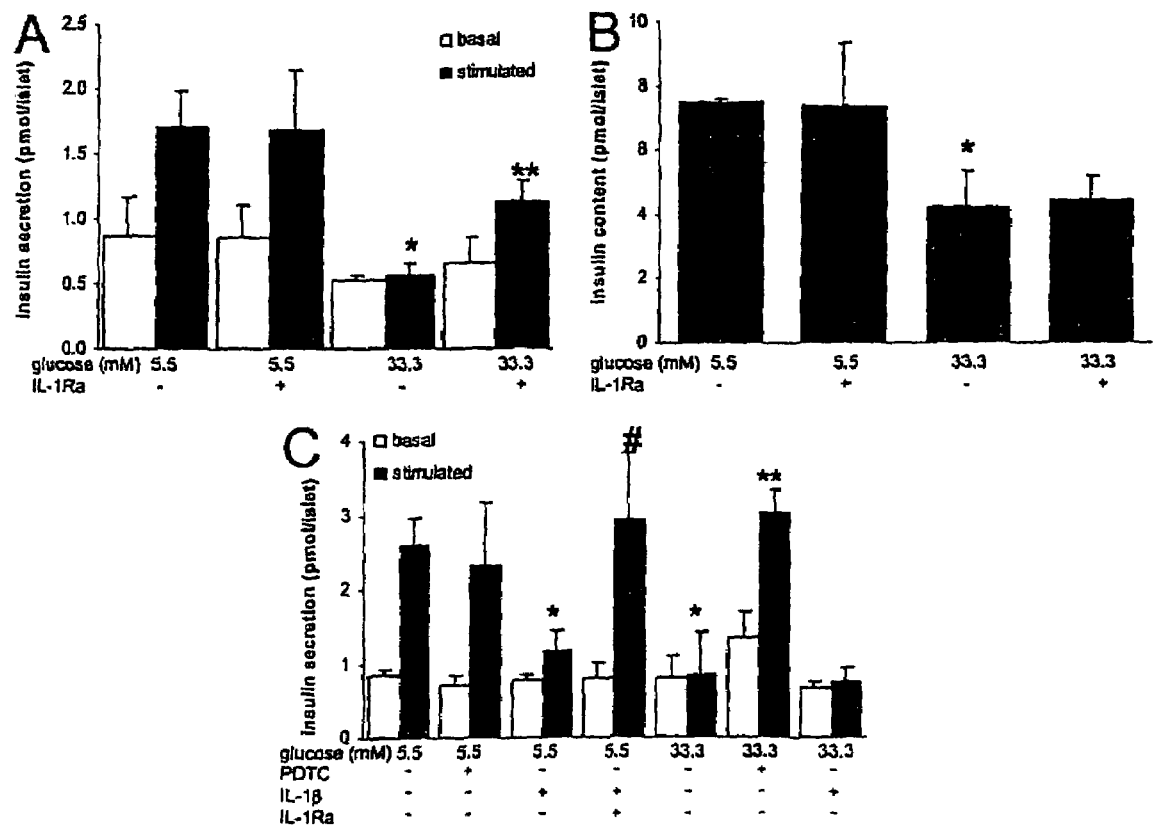

FIG. 6—IL-1Ra and PDTC restore glucose-stimulated insulin secretion in human islets exposed to high glucose.

Islets were cultured on extracellular matrix-coated dishes for 4 days in 5.5 and 33.3 mM glucose (control) or with IL-1Ra, PDTC, IL-1β in combination or individually. A, C, Basal and stimulated insulin secretion denotes the amount secreted during successive 1 h incubations at 3.3 and 16.7 mM glucose, respectively, following the 4 day culture period. B, Insulin content. Data are represented as the mean of three experiments±SE from three separate donors. In each experiment, the data were collected from three plates per treatment. *, P<0.01 relative to islets at 5.5 mM glucose; **, P<0.01 relative to islets at 33.3 mM glucose. *, P<0.01 relative to islets at 5.5 mM glucose plus IL-1β.

Figure 7:
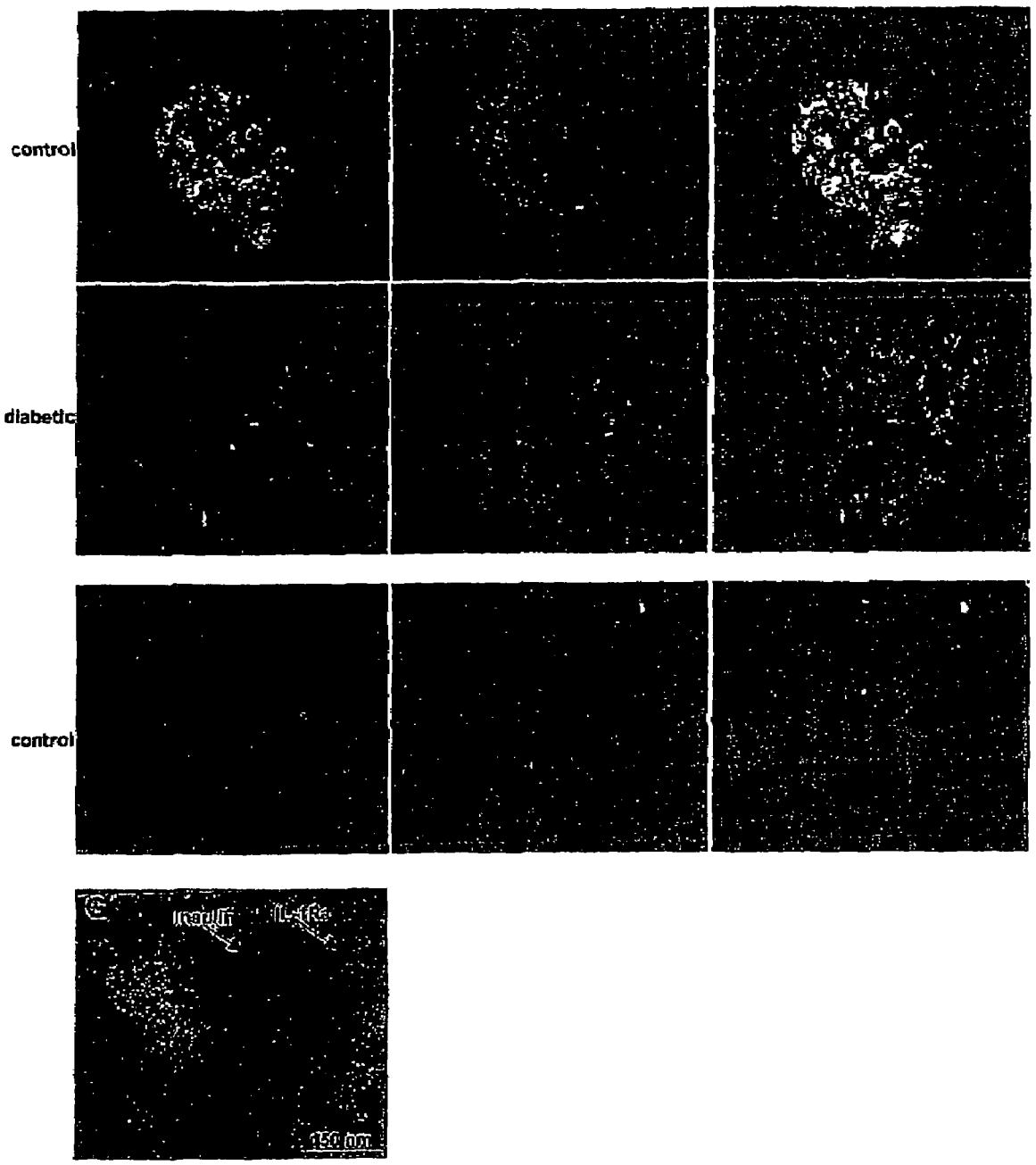

FIG. 7—IL-1Ra is expressed by human islets and down-regulated in type 2 diabetes.

Double immunostaining for IL-1Ra (A,C) or red (E) and insulin (B,D) or CD68 (F) in tissue sections of pancreases from a non-diabetic patient (A,B,E,F) and from a patient with type 2 diabetes (C,D). Magnification: ×250. (G) Electron microscopy of cultured human islets double gold-immunolabeled for insulin (small particles) and IL-1Ra (large particles).

Figure 8:
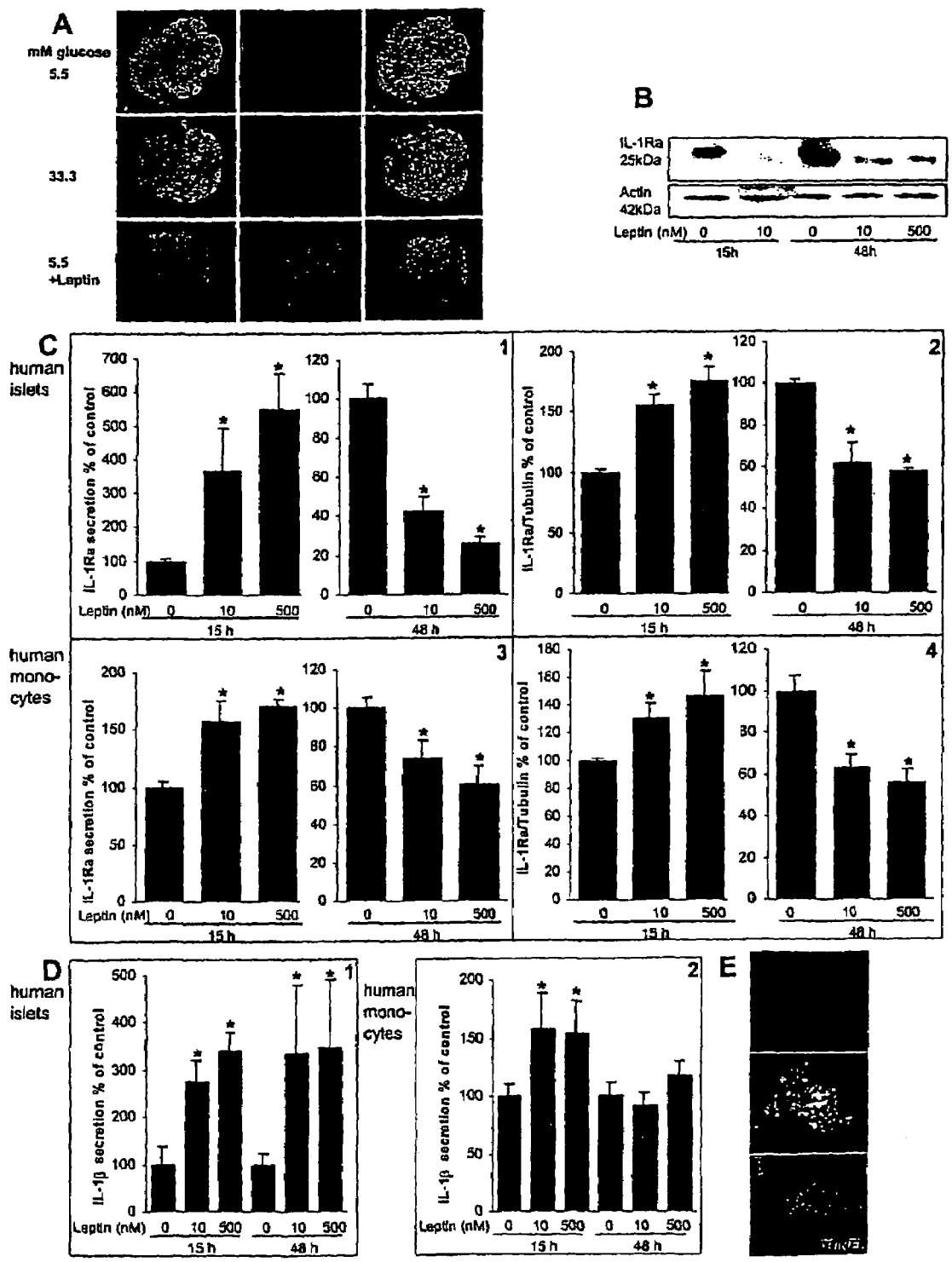

FIG. 8—Leptin decreases β-cell production of IL-1Ra and induces IL-1β release in human islets.

(A) Double immunostaining for IL-1Ra (1,3,5) and insulin (2,4,6) in sections of cultured human islets exposed for 48 h to media containing 5.5 mM glucose alone (1,2), 33.3 mM glucose (3,4) or 5.5 mM glucose and 10 nM leptin (5, 6). (B) Immunoblotting of IL-1Ra and actin. Human islets cultured in a suspension with and without 10 or 500 nM leptin were analyzed after 15 or 48 hours of incubation. The antibodies were blotted on the same membrane after stripping. One out of three experiments from three donors is shown. Each experiment displayed similar results. (C) Secretion of IL-1Ra (1,3) and RT-PCR detection and quantification of IL-1Ra mRNA expression (2,4). Supernatants and total RNA were obtained from human islets (1,2) and human blood monocytes (3,4) cultured for 15 and 48 hours in the presence of medium alone, 10 or 500 nM leptin. In the LightCycler quantitative PCR system, the level of IL-1Ra expression was normalized against tubulin, and the results were expressed as mRNA levels relative to control incubations. Data were collected from three tubes per treatment of five separate experiments from five islets donors and of three separate experiments from three blood monocytes donors. Results are means±SE of percentage relative to control incubations (100%, in absolute values for islets-IL-1Ra release: 7.43±0.69 pg/islet/24 h and for monocytes-IL-1Ra release: 48.2±0.9 ng/ml/24 h). *, P<0.01 compared to controls. (D) Secretion of IL-1β from human islets (1) and human blood monocytes (2) cultured for 15 and 48 hours in the presence of medium alone, 10 or 500 nM leptin. Data were collected from three tubes per treatment of five separate experiments from five islets donors and of three separate experiments from three monocytes donors. Results are mean±SE of percentage relative to control incubations (100%, in absolute values for islets-IL-1β release: 0.11±0.04 pg/islet/24 h and for monocytes-IL-1Ra release: 228.2±44.3 pg/ml/24 h). *, P<0.01 compared with controls. (E) Triple immunostaining for IL-1β (1), insulin (2) and DNA fragmentation by the TUNEL assay in black (3). The arrows mark a β-cell stained positive for IL-1β, insulin and the TUNEL reaction.

Figure 9:
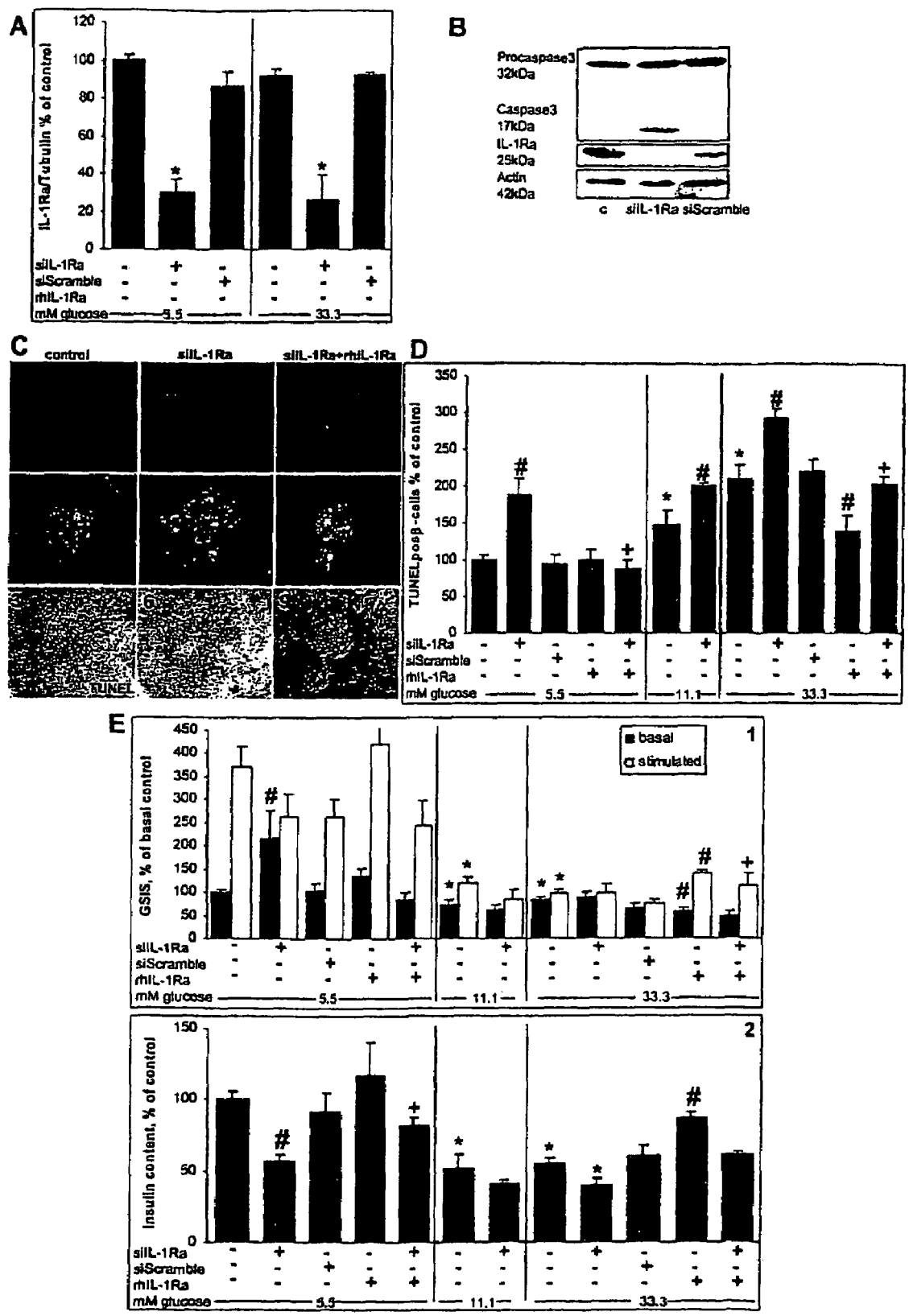

FIG. 9—Antagonizing IL-1Ra by siIL-1Ra induces β-cell apoptosis and impairs β-cell function.

(A) RT-PCR detection and quantification of IL-1Ra mRNA expression. Total RNA was isolated from human islets cultured for 48 hours in medium containing 5.5 or 33.3 mM glucose alone (controls) or after transfection with 50 nM siIL-1Ra or with 50 nM of a scrambled RNA sequence (siScramble) with or without addition of 500 ng/ml exogenous rhIL-1Ra. In the Light Cycler quantitative PCR system, the level of IL-1Ra expression was normalized against tubulin and the results expressed as mRNA levels relative to control incubations at 5.5 mM. Results are presented as means±SE of five independent experiments from five donors. *, P<0.001 compared to control islets at the same glucose concentration. (B) Immunoblotting of procaspase-3, activated caspase 3, IL-1Ra and actin. Human islets were cultured for 48 hours in medium containing 5.5 mM glucose alone or after transfection with 50 nM siIL-1Ra or with 50 nM siScramble. The antibodies were blotted on the same membrane after stripping. One out of four experiments from four donors is shown. Each experiment displayed similar results. (C,D,E) Human islets were cultured on extracellular matrix coated dishes for 4 days in 5.5, 11.1 and 33.3 mM glucose alone-(controls) or after transfection with 50 nM siIL-1Ra or 50 nM siScramble with or without addition of 500 ng/ml exogenous rhIL-1Ra. (C) Triple immunostaining for IL-1Ra (1,4,7), insulin (2,5,8) and DNA fragmentation by the TUNEL assay in black (3,6,9) in islets exposed to media containing 5.5 mM glucose alone (1, 2, 3) or with siIL-1Ra (4, 5, 6) or with siIL-1Ra and rhIL-1Ra (7,8,9). The arrows mark β-cell's nuclei stained positive for the TUNEL reaction. Note that TUNEL-positive β-cells are negative for IL-1Ra. (D) Results are means±SE of percentage of TUNEL-positive β-cells relative to control incubations at 5.5 mM glucose alone (100%, in absolute value: 0.33±0.03% TUNEL-positive β-cells). The mean number of islets scored from each donor was 44 (range 24-80) for each treatment condition. Islets were isolated from five organ donors. #, P<0.05 compared to control islets at the same glucose concentration; *, P<0.05 compared with islets at 5.5 mM glucose alone; +, P<0.05 compared to siIL-1Ra transfected islets alone at the same glucose concentration. (E) 1: basal and stimulated insulin secretion during successive 1-hour incubations at 3.3 (basal) and 16.7 (stimulated) mM glucose following the 4-day culture period. 2: insulin content. Data are presented as means±SE of three experiments from three separate donors. In each experiment, the data were collected from three plates per treatment. #, P<0.05 compared with control islets at the same glucose concentration; *, P<0.05 compared with islets at 5.5 mM glucose alone; +, P<0.05 compared to siIL-1Ra transfected islets alone at the same glucose concentration.

Figure 10:
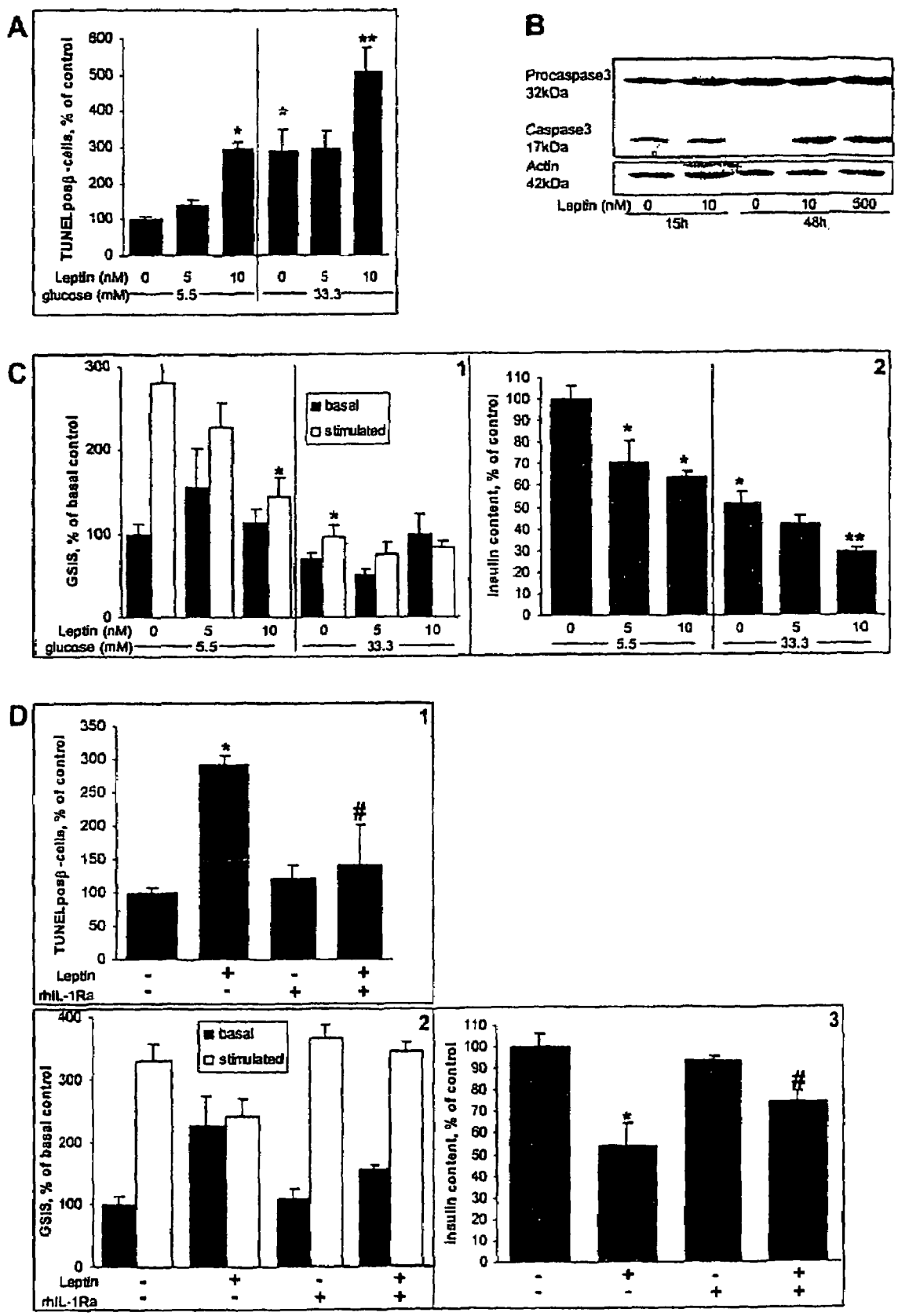

FIG. 10—Leptin induces β-cell apoptosis and impairs β-cell function via IL-1β-signaling.

(A) Human islets were cultured on extracellular matrix-coated dishes for 4 days in 5.5 and 33.3 mM glucose (controls) or with 5 and 10 nM Leptin. Results are means±SE of percentage of TUNEL-positive β-cells relative to control incubations at 5.5 mM glucose alone (100%, in absolute value: 0.35±0.04 TUNEL-positive % β-cells). The mean number of islets scored from each donor was 31 (range 21-45) for each treatment condition. Islets were isolated from five organ donors. *, P<0.01 compared with islets at 5.5 mM glucose alone; **, P<0.01 compared to islets at 33.3 mM glucose alone. (B) Immunoblotting of procaspase-3, activated caspase 3 and actin. Human islets were cultured for 15 and 48 hours in medium containing 5.5 mM glucose alone or with 10 or 500 nM leptin. The antibodies were blotted on the same membrane after stripping. One out of four experiments from four donors is shown. Each experiment displayed similar results. (C,D) Islets were cultured on extracellular matrix-coated dishes for 4 days in 5.5 and 33.3 mM glucose alone (controls) with or without 5 or 10 nM Leptin or with addition of 500 ng/ml exogenous rhIL-1Ra. (C) 1: basal and stimulated insulin secretion denote the amount secreted during successive 1-hour incubations at 3.3 (basal) and 16.7 (stimulated) mM glucose following the 4-day culture period. 2: insulin content. Data are represented as means±SE of three experiments from three separate donors. In each experiment, the data were collected from three plates per treatment. *, P<0.01 compared to islets at 5.5 mM glucose alone; **, P<0.01 compared to islets at 33.3 mM glucose alone. (D) 1: results are means±SE of the percentage of TUNEL-positive β-cells relative to control incubations at 5.5 mM glucose alone (100%, in absolute value: 0.37±0.06% TUNEL-positive β-cells). The mean number of islets scored from each donor was 29 (range 25-32) for each treatment condition. 2: basal and stimulated insulin secretion denotes the amount secreted during successive 1-hour incubations at 3.3 (basal) and 16.7 (stimulated) mM glucose following the 4 day culture period. 3: insulin content. Data are presented as means±SE of three experiments from three separate donors. In each experiment, the data were collected from three plates per treatment. *, P<0.01 compared to islets at 5.5 mM glucose alone; #, P<0.05 compared to leptin treated islets alone.

DETAILED DESCRIPTION OF THE INVENTION

In advanced stages of type 2 diabetes, the β-cell function often degenerates to such a degree that insulin therapy becomes necessary. The islet demise in humans with late type 2 diabetes is probably due to a combination of genetic and environmental components as well as to secondary events including hyperglycemia-induced impaired β-cell function and apoptosis. The hallmark of type 1 diabetes is a specific and massive destruction of the β-cells, mostly by apoptosis. Although both diseases have fundamental etiological differences, increasing evidence links both types of diabetes, and a significant fraction of individuals originally diagnosed with type 2 diabetes are cryptic type 1 diabetics or evolve with time to a type 1 state, and exhibit anti-β-cell autoimmunity (41-44). Moreover, apoptotic cells can provoke an immune response under the appropriate conditions, for example, when present in high enough numbers or exposed to cytokines such as IL-1β (45;46). Thus, induction of IL-1β by elevated glucose concentrations as shown in the present study or as part of an autoimmune response may connect type 2 and type 1 diabetes.

Resident islet macrophages are fundamental in the development of autoimmune diabetes (47;48). Activation of resident macrophages results in the expression and release of IL-1β (49). Recently, it has been shown that viral replicative intermediate double-stranded RNA stimulates rat islet β-cell production of IL-1, as a mechanism by which viral infection may mediate β-cell damage in autoimmune diabetes (50). Interestingly, this same study revealed that, following such stimulation, rat β-cells also produce IL-1 converting enzyme, the enzyme required for activation of IL-1β. The results presented in this study indicate that human β-cells themselves are capable of producing IL-1 independently of any viral infection or immune-mediated process, in response to glucose. The fact that IL-1β producing β-cells were also detected in tissue sections of type 2 diabetic patients and in hyperglycemic but not euglycemic Psammomys obesus fully supports the in vitro observations and the central hypothesis of this study.

Diabetes-prone Psammomys obesus, when fed a high-energy diet, develop diabetes. As in some humans with type 2 diabetes, initial hyperinsulinemia in this animal model of diabetes progresses to hypoinsulinemia at later stages of the disease due to insufficient insulin secretion and reduced pancreatic insulin reserve (51). In a longitudinal study, the present inventor and co-workers analyzed β-cell turnover during nutrition-induced diabetes (8). During the development of hyperglycemia an initial and transient increase in β-cell replication occurs, followed by a prolonged increase in the number of apoptotic β-cells. The present inventor and co-workers now extend this study by the observation of IL-1β expressing β-cells in parallel to insulin depletion in islets of hyperglycemic Psammomys obesus. Normalization of plasma glucose by treatment of the animals with phlorizin prevented IL-1β expression and restored insulin expression in the islets, suggesting that in addition to its role as a mediator of glucose-induced β-cell apoptosis, IL-1β may participate in control of pancreatic insulin reserve.

To the best of the inventor's knowledge, iNOS can not be induced by IL-1β alone in human islets (52;53). Moreover, cytokine-induced Fas expression is NO-independent (54;55). In line with these reports, glucose did not induce iNOS in the present study. Therefore, the IL-1β-mediated deleterious effects are probably NO-independent. However, it can not be excluded that NO is produced by β-cells in an iNOS-independent way, since IL-1β-induced nitrite has been demonstrated in the past (24;25;56), although this has not been observed by others (57).

At least 20 hours of exposure to high glucose are required to induce IL-1β, leading to NF-κB activation, Fas expression and β-cell death. This is in line with glucotoxic effects which appear only following prolonged exposure to high glucose.

Inhibition of NF-κB activation by an adenoviral vector encoding for the repressor I-κB protects human islets from Fas-triggered apoptosis and results in normal insulin response in the presence of IL-1β (56). Similarly, in purified rat β-cells, inhibition of cytokine-induced NF-κB activation prevents β-cell apoptosis (59). Thus, the present finding that glucose decreases IκB expression and induces NF-κB activation via IL-1β allows the prevention of glucotoxic effects by inhibition of NF-κB activation.

So far, IL-1β production and release by islets was considered to be limited to type 1 diabetes. Here, the present inventor and co-workers demonstrate that high concentrations of glucose induce IL-1β production and secretion in human β-cells, leading to Fas receptor up-regulation, NF-κB activation, β-cell apoptosis and dysfunction. Moreover, the present inventor and co-workers observed IL-1β producing β-cells in diabetic patients and diabetic Psammomys obesus. The pathway by which hyperglycemia causes impairment and loss of insulin producing cells thus shares features with immune-mediated processes. It follows that the pro-inflammatory cytokine IL-1β may be a crucial factor contributing to β-cell glucotoxicity in the pathogenesis of type 2 diabetes. The inventor believes that the new findings implicate that substances that inhibit the action of the members of the IL-1β/NF-κB pathway can be used to protect and preserve β-cell mass and function in prediabetic and diabetic type 2 patients.

Thus, the present invention i.a. relates to the use of an Interleukin 1 receptor antagonist (IL-1Ra) for the preparation of a medicament for the treatment or prophylaxis of type 2 diabetes in a mammal, such as a dog or a human, in particular a human.

Thus, it should be understood that the present invention is applicable for the treatment of patients already diagnosed as type 2 diabetes patients as well as for the prophylactic treatment of mammals predisposed, e.g. genetically, environmentally, dietarily or socially predisposed, to type 2 diabetes.

When used herein, the term "type 2 diabetes" is defined as a metabolic disorder characterized by hyperglycemia and abnormities in the glucose-protein- and lipid-metabolism. Type 2 diabetes is caused by insulin resistance which is not adequately compensated due to an insufficient β-cell secretory capacity.

Interleukin 1 receptor antagonist (IL-1Ra) is a mature glycoprotein of 152 amino acid (aa) residues. The protein has a native molecular weight of 25 kDa. When used herein, the terms "Interleukin 1 receptor antagonist" and "IL-1Ra", and the like, are intended to encompass wild-type Interleukin 1 receptor antagonists as well as polypeptides exhibiting substantially the same or improved biological activity relative to the wild-type Interleukin 1 receptor antagonists. Such polypeptides include, without limitation, Interleukin 1 receptor antagonists that have been chemically modified, and Interleukin 1 receptor antagonist variants into which specific amino acid sequence alterations have been introduced that modify the bioactivity of the polypeptide. It further encompasses polypeptides with a slightly modified amino acid sequence, e.g., polypeptides having a modified N-terminal end including N-terminal amino acid deletions or additions, and polypeptides having a modified C-terminal end including C-terminal amino acid deletions or additions.

IL-1Ra can be obtained from natural sources, e.g. by extraction and purification from tissue or body fluids of mammals, such as humans, pork, goats, sheep, etc.; or by recombinant cell culture systems.

In one embodiment, the Interleukin 1 receptor antagonist (IL-1Ra) is a recombinant protein (rIL-1Ra). In a more specific embodiment, the Interleukin 1 receptor antagonist (IL-1Ra) is a recombinant human protein (rhIL-1Ra).

As an example of a suitable IL-1Ra should be mentioned the medicament Kineret® (anakinra) which is a recombinant, nonglycosylated form of the human interleukin 1 receptor antagonist (hIL-1Ra). Kineret® differs from native human IL-1Ra in that it has the addition of a single methionine residue at its N-terminal end. Kineret® consists of 153 amino acids and has a molecular weight of 17.3 kilodaltons. It is produced by recombinant DNA technology using an *E. coli* bacterial expression system. Kineret® is supplied in single use 1 mL prefilled glass syringes with 27 gauge needles as a sterile, clear, colorless-to-white, preservative-free solution for daily subcutaneous (SC) administration. Each 1 mL prefilled glass syringe contains: 0.67 mL (100 mg) of anakinra in a solution (pH 6.5) containing sodium citrate (1.29 mg), sodium chloride (5.48 mg), disodium EDTA (0.12 mg), and polysorbate 80 (0.70 mg) in Water for Injection, USP.

As another examples of a commercially available IL-1Ra can be mentioned the recombinant porcine IL-1Ra provided by R&D Systems Inc., Minneapolis, Minn., USA; Catalog No. 780-RA.

In an embodiment of the invention, the medicament comprises IL-1Ra in combination with pyrrolidinedithiocarbamate (PDTC).

A further embodiment of the invention relates to the use of the NF-κB inhibitor pyrrolidinedithiocarbamate (PDTC) for the preparation of a medicament for the treatment or prophylaxis of type 2 diabetes in a mammal, such as a dog or a human, in particular a human.

The medicament comprising IL-1Ra and/or pyrrolidinedithiocarbamate (PDTC) is preferably administered parenterally, such as subcutaneously, intramuscularly or intravenously. General methods for the formulation of IL-1Ra and/or pyrrolidinedithiocarbamate (PDTC) can be found in Remington: The Science and Practice of Pharmacy by Alfonso R. Gennaro (Editor), Lippincott, Williams & Wilkins; Dec. 15, 2000; ISBN: 0683306472.

The medicament comprising IL-1Ra and/or pyrrolidinedithiocarbamate (PDTC) is preferably formulated with a pharmaceutically acceptable carrier, e.g. adapted for parenteral administration, such as subcutaneous, intramuscular or intravenous administration.

The term "pharmaceutically acceptable carrier" is intended to encompass media generally acceptable for use in connection with the parenteral administration of biologically active agents to a mammal such as a human. Pharmaceutically acceptable carriers are generally formulated according to a number of factors well within the purview of the ordinary skilled artisan to determine and account for, including without limitation: the particular active drug substance(s) (IL-1Ra and/or pyrrolidinedithiocarbamate (PDTC)), its/their concentration, stability and intended bioavailability; the subject, its age, weight and general condition; and the intended route of administration of the composition, e.g. subcutaneous, intraperitoneal, intraveneous, or intramuscular. Typical pharmaceutically acceptable carriers used in parenteral drug administration include, e.g., D5W (an aqueous solution containing 5% weight by volume of dextrose, and physiological saline. Pharmaceutically acceptable carriers can contain additional ingredients, e.g. those which enhance the stability of the active drug substance(s) included, such as preservatives and antioxidants.

A medicament for parenteral use (in particular subcutaneous, intraveneous, or intramuscular use) typically comprises 0.1 to 1000 mg of the active drug substance(s) per kg of the mammal's body.

The medicament for use in the context of the invention may comprise the active drug substance(s) in the form of a sterile injection. To prepare such a composition, the active drug substance(s) is/are dispersed or dissolved in a pharmaceutically acceptable carrier which conveniently may comprise suspending, solubilising, stabilising, pH-adjusting and/or dispersing agents. Among acceptable carriers that may be employed are water, water adjusted to a suitable pH by addition of an appropriate amount of an acid (e.g. hydrochloric acid), a base (e.g. sodium hydroxide), or a suitable buffer, 1,3-butanediol, Ringer's solution and isotonic sodium chloride solution. The aqueous formulation may also contain one or more preservatives, e.g., methyl, ethyl or n-propyl p-hydroxybenzoate.

In view of the above, it should be apparent that the present invention also provides a method of treating or prophylactically suppressing type 2 diabetes, the method comprising administering to a mammal in need thereof a sufficient amount of an Interleukin 1 receptor antagonist (IL-1Ra). Furthermore, the present invention provides a method of treating or prophylactically suppressing type 2 diabetes, the method comprising administering to a mammal in need thereof a sufficient amount of pyrrolidinedithiocarbamate (PDTC). The above embodiments and preferences apply mutatis mutandis.

The applicability of IL-1Ra and/or pyrrolidinedithiocarbamate for the treatment or prophylaxis of type 2 diabetes can be confirmed by animal model studies or clinical studies as described in the examples section.

EXAMPLES

Methods

Islet isolation and culture. Islets were isolated from pancreases of eleven organ donors at the Department of Surgery, University of Geneva Medical Center, as described (32-34). The islet purity was >95%, as judged by dithizone staining (if this degree of purity was not primarily achieved by routine isolation, islets were handpicked). The donors, aged 40-70 years, were heart-beating cadaver organ donors, and none had a previous history of diabetes or metabolic disorders. For long-term in vitro studies, the islets were cultured on extracellular matrix-coated plates derived from bovine corneal endothelial cells (Novamed Ltd., Jerusalem, Israel), allowing the cells to attach to the dishes and spread, preserving their functional integrity (7;35). Islets were cultured in CMRL 1066 medium containing 100 U/ml penicillin, 100 μg/ml streptomycin and 10% fetal calf serum (Gibco, Gaithersburg, Md.), hereinafter referred to as culture medium. Two days after plating, when most islets were attached and began to flatten, the medium was changed to culture medium containing 5.5, 11.1 or 33.3 mM glucose. In some experiments, islets were additionally cultured with 2 ng/ml recombinant human IL-1β, 1000 U/ml recombinant human IFNγ (ReproTech EC Ltd, London, UK), 500 ng/ml IL-1β receptor antagonist (IL-1Ra) (R&D Systems Inc., Minneapolis, Minn.), 1 ng/ml membrane bound Fas-ligand (FasL) (36) (upstate biotechnology, Lake Placid, N.Y.) or with 100 μM pyrrolidinedithiocarbamate (PDTC; Sigma; 2 h per 2 d of culture).

Animals. *Psammomys obesus* of both sexes (age 2.0-3.5 months) from the diabetes-prone and diabetes-resistant lines of the Hebrew University colonies were obtained from Harlan (Jerusalem, Israel). After weaning, diabetes-prone *Psammomys obesus* were maintained on a low-energy diet containing 2.38 kcal/g (Koffolk, Petach Tikva, Israel) until the start of the experiments, whereas diabetes-resistant *Psammomys obesus* were maintained on a high-energy diet containing 2.93 kcal/g (Weizmann Institute, Rehovot, Israel) to identify animals that develop diabetes and exclude them from the study (~30-40% of the animals in the diabetes-resistant colony). All non-fasted animals with random blood glucose concentrations <7.8 mmol/l (Glucometer Elite, Bayer Diagnostics, Elkart, Ind.) were considered nondiabetic. Diabetes-prone *Psammomys obesus* switched to a high-energy diet, received an injection of 0.4 g/kg phlorizin (Sigma) or solvent (40% propylene glycol) every 12 h and were killed after 8 days. *Psammomys obesus* were anesthetized with ketamine (Ketalar, Park-Davis, Gwent, U.K.) and exsanguinated by cardiac puncture. The pancreas was rapidly removed, and immersion-fixed in 10% phosphate-buffered formalin. The animal studies were approved by the Institutional Animal Care and Use Committee of the Hebrew University and the Hadassah Medical Organization.

Detection of IL-1β expressing β-cells. Pancreases from routine necropsies and pancreases from *Psammomys obesus* were immersion-fixed in formalin, followed by paraffin embedding. Sections were deparaffinized and rehydrated, and endogenous peroxidase blocked by submersion in 0.3% $H_2O_2$ for 15 min. Sections were then incubated in methanol for 4 min. After washing with PBS, cultured islets and isolated β-cells were fixed in 4% paraformaldehyde (30 min, room temperature) followed by permeabilisation with 0.5% triton X-100 (4 min, room temperature). Both tissue sections and cultured cells were double-labeled for IL-1β and insulin by 1 h exposure to 10% bovine serum albumin, followed by incubation (1 h, 37° C.) with mouse anti-IL-1β antibody (1:30 dilution, R&D Systems Inc.). Detection was performed using donkey anti-mouse Cy3 conjugated antibody (1:100 dilution, Jackson). Subsequently, specimens were incubated for 30 min at 37° C. with guinea pig anti-insulin antibody diluted 1:50 (Dako, Carpinteria, Calif.), followed by a 30 min incubation with a 1:20 dilution of fluorescein-conjugated rabbit anti-guinea pig antibody (Dako). For positive control of IL-1β staining, human mononuclear cells were isolated as described previously (37) and exposed for 2 h, 37° C. to 1 μg/ml lipopolysaccharide (Difco, Detroit, Ind.). Coverslips were air dried and mounted onto slides, fixed and permeabilized for 5 minutes at room temperature in 50% acetone/methanol and stained for IL-1β as described.

For mRNA in situ hybridization of IL-1β, DNA templates were generated by polymerase chain reaction with incorporation of a T3 or a T7 promotor into the antisense or sense primer. The following primers were used:

nol/chloroform purification, Digoxigenin-labeled RNA probes were prepared using RNA T7- and T3-polymerase and RNA Digoxigenin labeling mix (Roche, Switzerland). Tissue sections were treated with 20 μg/ml Proteinase K (Roche) and prehybridized for 2 hours at 55° C. in hybridization buffer containing 50% formamide, 5× sodium chloride-sodium citrate, 50 μg/ml salmon sperm (Sigma), 1× Denhart's solution, 250 μg/ml RNA Type IV from calf liver (Sigma). The hybridization was performed overnight at 52° C. in 100 μl hybridization buffer containing 30 ng of Digoxigenin-labeled RNA probe. Sections were then blocked with 5% milk powder at room temperature and incubated 1 hour at 37° C. with anti-digoxigenin-rhodamine Fab fragment (20 μg/ml; Roche), followed by insulin immunostaining as described above. After staining, samples were embedded in Kaiser's glycerol gelatin (Merck, Darmstadt, Germany) and analyzed by light and fluorescence microscopy (microscope Axiolab; Zeiss, Jena, Germany).

Western blot analysis. Islets were cultured in a culture medium in non-adherent plastic dishes. One day after isolation, the medium was changed and groups of 200 islets were incubated for 44 hours in culture medium containing 5.5 or 33.3 mM glucose without or with 2 ng/ml IL-1β or 500 ng/ml IL-1Ra. At the end of the incubations, islets were washed in PBS, suspended in 50 μl sample buffer containing 125 mM Tris-HCl, pH 6.8, 4% SDS, 10% glycerol, 0.3% bromphenol blue, 1.8% β-mercaptoethanol and boiled for 5 min. Equivalent amounts of each treatment group were run on 15% SDS polyacrylamide gels. Proteins were electrically transferred to nitrocellulose filters and incubated with rabbit anti-Fas (C20, Santa Cruz Biotechnology Inc., Santa Cruz, Calif.), mouse anti-IL-1β (R&D Systems Inc), rabbit anti-IL-1β (recognizing precursor and cleaved forms of human IL-1β; Cell Signaling, Beverly, Mass.), mouse anti-NF-κB (p65) (Active Motif, Carlsbad, Calif.), mouse anti-NOS-2 (C-11, recognizing mouse, rat and human origin of inducible nitric oxide synthase (iNOS), Santa Cruz Biotechnology Inc.) or mouse anti-actin (C-2; Santa Cruz Biotechnology Inc.) antibodies, followed by incubation with horseradish-peroxidase-linked anti-mouse or anti-rabbit IgGs (Santa Cruz Biotechnology Inc.). The emitted light was captured on X-ray film after adding Lumiglo reagent (Phototope-HRP Western blot detection kit; Biolabs, Beverly, Mass.). As a marker, biotinylated protein molecular weight standard (Biolabs) was run in parallel. Between the incubations, nitrocellulose membranes were stripped for 30 min at 50° C. in 40 ml of a solution containing 280 μl β-mercaptoethanol, 5 ml 0.5 M Tris-HCl, pH 6.8 and 10% SDS, and then they were washed for 1 h in Tris-buffered saline containing 0.1% Tween-20. Intensity of bands was analyzed using Multianalyst™ (Bio Rad, Laboratories inc., Hercules, Calif.).

NF-κB activation. Islets were cultured in a suspension as described above and washed with PBS. Activation of NF-κB complex was quantified with an ELISA-based Kit, using attached oligonucleotides binding to a NF-κB consensus site and detected by an anti-p65 or p50 subunit antibody, accord-

```
T3  5'AAGCGCGCAATTAACCCTCACTAAAGGGTCAGCACCTCTCAAGCAGAA3'
and

T7  5'GGCCAGTAATTGTAATACGACTCACTATAGGGAGGCGGCCCTGAAAGGAGAGAGCTGA3'.
```

Purification of PCR product was performed with Nucleospin Extract 2 in 1™ (Machery-Nagel, Düren, Germany) according to the manufacturer's instruction. After pheing to the manufacturer's instructions (Trans-AM™ NFκB, Active Motif). In parallel, islets were fixed in Bouin solution for 15 min, resuspended in 40 μl of 2% melted agarose in PBS (40° C.), followed by rapid centrifugation and paraffin embedding. Sections were deparaffinized and rehydrated, endogenous peroxidase blocked by submersion in 0.3% $H_2O_2$ for 15 min and incubated in methanol for 4 min. Sections were incubated with mouse anti-NF-κB (p65) (1:50 dilution) or rabbit anti-IκB (1:50 dilution, C-21, Santa Cruz) antibodies, detected by donkey anti-mouse or anti-rabbit Cy3 conjugated antibodies and double stained for insulin as described above.

RNA extraction, RT-PCR and sequencing of RT-PCR product. Islets were cultured in a suspension as described above. Total RNA was extracted using Rneasy mini kit (Qiagen, Basel, Switzerland) and RT-PCR was performed using the Superscript™ II Rnase H Reverse transcriptase KIT and oligo-dT(24) (Life technologies, Gibco) according to the instructions from the manufacturers. The primers were 5'AAGCTGATGGCCCTAAACAG3'/5'AGGTGCATCGT-GCACATAAG3' (human IL-1β), 5'GCATCTGGACCCTC-CTACCT3'/5'CAGTCTGGTTCATCCCCATT3' (human Fas) and 5'acgtgcgttactccaccaaca375'catagcggatgagctgagcatt3' (human iNOS). The conditions of the PCR amplification for IL-1β and Fas were: denaturation 30 seconds at 94° C., annealing 30 seconds at 60° C. and elongation 30 seconds at 72° C., followed for real time PCR by quantification 5 seconds at 80° C., 45 cycles. The saturation of the PCR amplification occurred between 22 and 28 cycles. The size of the PCR amplification products was 250 bp. The purified PCR products were sequenced to confirm amplification of the correct gene. The conditions of the PCR amplification for iNOS were: denaturation 30 seconds at 94° C., annealing 40 seconds at 55° C. and elongation 30 seconds at 72° C., 35 cycles. For quantitative analysis, we used the Light Cycler quantitative PCR system (Roche, Basel, Switzerland) and performed quantitative PCR with a commercial kit (Light Cycler-DNA Master SYBR Green I; Roche). The amount of Fas and IL-1β mRNA was standardized against GAPDH (5'AACAGCGACACCCACTCCTC3'/

5'GGAGGGGAGATTCAGTGTGGT3').

β-cell apoptosis. The free 3-OH strand breaks resulting from DNA degradation were detected by the terminal deoxynucleotidyl transferase-mediated dUTP nick-end labeling (TUNEL) technique (38). After washing with PBS, cultured islets were fixed in 4% paraformaldehyde (30 min, room temperature) followed by permeabilisation with 0.5% triton X-100 (4 min, room temperature). The TUNEL assay was performed according to the manufacturer's instructions (In Situ Cell Death Detection Kit, AP; Boehringer Mannheim, Germany). The preparations were then rinsed with Tris-buffered saline and incubated (10 min, room temperature) with 5-bromo-4-chloro-indolyl phosphate/nitro blue tetrazolium liquid substrate system (Sigma). Then, islets were incubated with a guinea pig anti-insulin antibody as above, followed by detection using the streptavidin-biotin-peroxidase complex (Zymed). In parallel to the TUNEL reaction, we used the DNA-binding dye propidium iodide (Sigma) to assess the effects of glucose on necrosis. Cultured islets were washed with PBS (without paraformaldehyde-fixation), incubated for 10 min on ice with 10 µg/ml propidium iodide in PBS, washed with PBS, and embedded in Dako fluorescent mounting medium (Dako). The samples were immediately evaluated by fluorescence microscopy for positively stained necrotic nuclei.

Cytokine release. Cytokines release was evaluated in the culture medium collected before the termination of each experiment. The following kits were used: human IL-1α, IL-1β, and IL-12 ELISA (R&D Systems Inc.), human TNFα ELISA (Endogen, Boston, Mass.), human IFNγ ELISA (Gibco).

Insulin release and content. To determine acute insulin release in response to glucose stimulation, islets were washed in RPMI 1640 medium with 10% FCS and containing 3.3 mM glucose and pre-incubated for 1 h in the same medium. The medium was then discarded and replaced with fresh medium containing 3.3 mM glucose for 1 h for basal secretion, followed by an additional 1 h incubation in medium containing 16.7 mM glucose. Incubates were collected and frozen for insulin assays. Then, islets were washed with PBS and extracted with 0.18 N HCl in 70% ethanol for 24 h at 4° C.; the acid-ethanol extracts were collected for determination of insulin content. Insulin was determined by a human insulin RIA kit (CIS bio international, Gif-Sur-Yvette, France).

Evaluation and statistical analysis. Samples were evaluated in a randomized manner by a single investigator (K.M.) who was blinded to the treatment conditions. Care was taken to score islets of similar size. Some larger islets did not completely spread and were several cells thick. Such larger islets were excluded because a monolayer is a prerequisite for single cell evaluation. The mean surface of the evaluated islet-monolayers was 0.031+/−0.012 $mm^2$ and 0.029+/−0.011 $mm^2$ in islets cultured at 5.5 and 33.3 mM glucose, respectively (n. s.). Thus, the exclusion of larger islets occurred to a similar extent in each dish independently of the treatment. Saisam™ software (Microvision instruments, Evry, France) was used to measure the areas. Data were analyzed by student's t test or by analysis of variance with a Bonferroni correction for multiple group comparisons.

Results

Glucose induces IL-1β production and release in human islets. Human islets were exposed to elevated glucose concentrations for 4 days. Measurement of the IL-1β released in the culture medium revealed a 2.2-fold increase in islets cultured at 33.3 mM, relative to 5.5 mM glucose (FIG. 1A). To exclude a nonspecific effect of this high concentration of D-glucose, osmolarity was corrected with 27.8 mM L-glucose together with 5.5 mM D-glucose resulting in a similar release of IL-1β to that observed at 5.5 mM D-glucose alone. No IL-1β was detectable in unused culture medium. The specificity of IL-1β release was assessed by comparison with the release of other cytokines. A limited amount of IL-1α and TNFα was found, but neither was regulated by glucose and no significant amount of IFNγ or IL-12 was detectable (Table 1). The time-course of the effect of 33.3 mM glucose on IL-1β secretion revealed a significant effect only after 20 hours of exposure to high glucose, persisting after 44 hours (FIG. 1B). Western blot analysis and quantitative RT-PCR measurement of IL-1β production in human islets revealed that elevated glucose concentration induces not only IL-1β-release but also IL-1β-protein and -RNA synthesis (FIGS. 1C & D). Note however, that Western blot analysis gave quite variable results in terms of increased IL-1β in response to glucose. This may be due to varying numbers of non-endocrine cells (including most notably macrophages) in the different islet preparations. In the event of IL-1β production from such accompanying cells not being stimulated by glucose, it is found that the higher they are to total IL-1β production, the lower the expected glucose effect.

TABLE 1

Cytokines released by human islets cultured
at low and high glucose concentrations

| Cytokine (pg/islet) | 5.5 mM glucose | 33.3 mM glucose |
|---|---|---|
| IL-1α | 0.71 ± 0.76 | 0.68 ± 0.67 |
| IL-12 | <0.06 | <0.06 |
| TNFα | 5.68 ± 1.7 | 5.81 ± 1.96 |
| IFN-γ | <0.04 | <0.04 |

Human islets were cultured for 4 days in 5.5 or 33.3 mM glucose. Each number represents the mean of eight experiments±SE from eight separate donors.

Identification of the islet cellular source of glucose-dependent IL-1β production. We next identified the islet-cells producing IL-1β. Exposure of cultured human islets to 33.3 mM glucose for 4 days induced IL-1β expression in clusters of β-cells, as determined by double-immunostaining of islets plated on extracellular matrix-coated dishes with anti-IL-1β and anti-insulin antibodies (for representative images from one experiment out of six from six donors see FIG. 2A-D. In each experiment, IL-1β positive β-cells were observed in islets cultured at 33.3 mM glucose). To exclude false-positive results due to IL-1β secreted by other cells binding to β-cell membranes, islets were treated with IL-1Ra. Under these conditions, IL-1Ra should antagonize the interaction of IL-1β with its surface receptors on β-cells. Co-incubation with IL-1Ra displayed similar results, confirming β-cell production of IL-1β.

IL-1β is not expressed in normal human pancreatic islets (28). However, based on the in vitro studies it was anticipated that it might be expressed in islets of patients with type 2 diabetes, as a result of hyperglycemia. Expression of IL-1β was therefore studied in sections of pancreases from five poorly controlled type 2 diabetic patients, all with documented fasting blood glucose >8 mM. Double-immunostaining of the pancreatic sections for IL-1β and insulin revealed localization of IL-1β to clusters of β-cells in all pancreases (22.5+/−3.4% of the islets per pancreas exhibited clusters of IL-1β expressing β-cells. For representative images, see FIG. 2G-H). The presence of IL-1β mRNA transcripts was verified by in situ hybridization in β-cells of diabetic patients (FIG. 2K-L). IL-1β expression could not be detected in β-cells of non-diabetic controls (FIGS. 2E-F & I-J) and in the exocrine pancreas. A digoxigenin-labeled sense probe was used as control and gave no signal (FIG. 2N).

β-cell expression of IL-1β during development of diabetes in *Psammomys obesus* is glucose-dependent. To examine whether induction of IL-1β in vivo is also regulated by glucose, 3 diabetes-resistant and eight diabetes-prone *Psammomys obesus* fed a low or high-energy diet were studied and the hyperglycemic animals further treated with phlorizin, which corrects hyperglycemia by inhibiting renal tubular reabsorption of glucose. No IL-1β expressing β-cells were observed in islets of diabetes-resistant and in fasted diabetes-prone *Psammomys obesus* (for representative images see FIG. 3A-B). After 8 days of a high-energy diet, islets of severely hyperglycemic diabetes-prone *Psammomys obesus* exhibited IL-1β expression in most β-cells, which barely expressed insulin (FIG. 3C-D). Normalization of blood glucose by injection of phlorizin in animals fed a high-energy diet, restored insulin stores and prevented IL-1β expression (FIG. 3E-F).

IL-1β mediates glucose-induced NF-κB activation, Fas expression and β-cell apoptosis. The functional role of glucose-induced IL-1β was tested using IL-1Ra as an inhibitor. In human islets, elevated glucose concentrations induced a 1.9-fold increase in NF-κB activity (FIG. 4A). This was prevented by IL-1Ra. The effect of glucose on NF-κB activation was verified by Western blot analysis using an anti-NF-κB (p65) antibody, which exclusively recognizes the p65 subunit of the active nuclear form of the NF-κB transcription factor complex (39) (FIG. 4B). NF-κB is bound in the cytoplasm to inhibitory κB (IκB) proteins (40). Exposure of human islets to 33 mM glucose decreased IκB expression (FIG. 4C) leading to nuclear apparition of NF-κB (p65) in β-cells (FIG. 4D). Glucose-dependent induction of Fas-receptor protein and mRNA were also hindered by IL-1Ra (FIGS. 4B, E & F). Next, the ability of IL-1Ra to protect the β-cells from glucose-induced apoptosis was evaluated. Exposure of human islets cultured on extracellular matrix dishes to elevated glucose concentrations increased the number of nuclei displaying DNA fragmentation (TUNEL-positive) (FIG. 4G, H). Exposure of islet cultures for 4 days to increasing glucose concentrations (from 5.5 to 33.3 mM) did not, however, lead to propidium iodide uptake, thereby excluding necrosis. IL-1Ra did not significantly change baseline apoptosis at 5.5 mM glucose. However, IL-1Ra protected the β-cells from apoptosis induced by 33.3 mM glucose (FIG. 4G). Similarly, the NF-κB inhibitor PDTC inhibited glucose induced DNA fragmentation (FIG. 4H). Addition of exogenous FasL did not lead to a significant increase of β-cell death (2.8+/−0.4-fold increase of TUNEL-positive β-cells in 33.3 mM glucose alone vs. 3.0+/−0.4-fold increase in 33 mM glucose+exogenous FasL, as compared to control at 5.5 mM glucose). Finally, it was examined whether high glucose induces iNOS expression. Neither 33 mM glucose nor IL-1β alone induced iNOS mRNA (FIG. 5) or protein expression.

IL-1Ra and PDTC improve impaired β-cell function due to IL-1β mediated "glucotoxicity". Chronic exposure of human islets to 33.3 mM glucose or IL1β for 4 days abolished acute glucose-stimulated insulin release (FIGS. 6A & C). Co-incubation with IL-1Ra or PDTC partially restored such glucose stimulation. Insulin content of islets cultured at high glucose decreased compared to control (5.5 mM glucose), and remained unaffected by IL-1Ra (FIG. 6B).

Animal Study. Treatment of *Psammomys obesus*, an Animal Model of Type 2 Diabetes Mellitus, with Interleukin-1 Receptor Antagonist. (Suggested Study)

The therapeutic potential of exogenous administration of IL-1Ra to prevent the decline of β-cell mass observed in type 2 diabetes patients will be tested in *Psammomys obesus*. The gerbil *Psammomys obesus* shows insulin resistance and develops diet-induced obesity-linked diabetes, initially associated with hyperinsulinemia, and gradually progressing to hypoinsulinemia and severe hyperglycemia. This is accompanied by a transient increase in beta-cell proliferative activity and by a prolonged increase in the rate of beta-cell death, culminating in disruption of islet architecture (8). Because of the obvious similarities, it serves as a convenient model for human type 2 diabetes. We will explore whether treatment with IL-1Ra may prevent hyperglycemia-induced 1-cell apoptosis and impaired proliferation in pancreatic islets of *Psammomys obesus* during development of diabetes. As a part of an ongoing collaboration with the group of N. Kaiser (Hadassah University Hospital, Jerusalem), 10 mg/Kg body wt/d of IL-1Ra (Kinerete®) will be injected intraperitoneally to *Psammomys obesus*. The study will comprise 3 groups of diabetes-prone *Psammomys*:

Group 1, *Psammomys* maintained on low-energy diet.
Group 2, *Psammomys* treated with IL-1Ra and switched from low-energy to high-energy diet to induce diabetes.

Group 3, *Psammomys* treated with solvent and switched from low-energy to high-energy diet to induce diabetes.

Four animals of each group will be sacrificed on days 4, 7, 14, 21 and 28 of the study. Upon sacrifice, blood will be collected and used for measurement of plasma glucose, insulin and triglycerides. The pancreas will be removed and the head-portion frozen at −70° C. for subsequent determination of insulin content. The remaining tail-part will be fixed in 10% phosphate buffered formalin, followed by standard paraffin embedding. Sequential sections will be analyzed for expression of Fas, IL-1β, insulin as well as for β-cell proliferation and apoptosis. The proposed number of animals and the duration of the treatment are based on our previous studies with *Psammomys* (8).

Anticipated Conclusion

Assuming that glucotoxicity will be completely blocked by IL-1Ra, the following improvements can be expected in IL-1Ra treated animals as compared to placebo-treated:

Prevention or delay of diabetes onset

Protection from hyperglycemia-induced β-cell apoptosis, impaired proliferation and decreased β-cell mass.

Normalisation of pancreatic insulin content.

Clinical Study. Treatment of Patients with Type 2 Diabetes Mellitus with Interleukin-1 Receptor Antagonist. (Suggested Study)

72 patients will be randomised according to a double-blind, placebo-controlled protocol in which half of the patients are treated with IL-1Ra, the other half with saline. The treatment period will last 13 weeks. This time-period should be sufficient for reversal of functional glucotoxicity (61) and feasible in terms of patient compliance. Whether 13 weeks of treatment will be sufficient to make significant changes in β-cell mass is unpredictable. However, blocking β-cell apoptosis, while new islet formation and β-cell replication are normal (62), may initiate enlargement of β-cell mass, which may progress beyond the treatment period. Patient evaluation will be performed at start and after 4, 13, 26, 39 and 52 weeks. Following 13 weeks, patients with a fasting plasma glucose levels >8 mM or with a glycosylated hemoglobin level (HbA1c)>8% will be treated with insulin. Insulin treatment will not be initiated earlier to avoid interference with possible effects of insulin on primary outcome in the period where the largest effect of IL-1Ra are expected. To assess effects of IL-1Ra on insulin sensitivity, a subset of 40 patients (20 IL-1Ra- and 20 placebo-treated) will undergo an euglycemic-hyperinsulinemic clamp as well as a muscle and fat biopsy at start and after the end of treatment (13 weeks).

Inclusion Criteria:
Age>30
Diabetes mellitus Type 2 (American Diabetes Association criteria) of at least 3 months duration and treated solely with diet and exercise and/or oral antidiabetic drugs.
HbA1c>8%
Body-mass index (BMI)>27

Exclusion Criteria
Positive GAD 2 or IA-2 antibodies
HbA1c>12%, polyuria and thirst (exclusion of severely decompensated patients)
Current treatment with insulin
Established anti-inflammatory therapy
CRP>30 mg/dl, fever, current treatment with antibiotics, or chronic granulomatous infections (e.g. tuberculosis) in the history or on a screening chest X-ray.
Neutropenia or anemia (leucocyte count <2.0×10$^9$/l, haemoglobin<11 g/dl for males or <10 g/dl for females)
Pregnancy or breast-feeding
Severe liver or renal disease (AST or ALT>3 times the upper limit of normal laboratory range, serum creatinine >130 μM)
Ongoing malignant neoplasm
Use of any investigational drug within 30 days of enrolment into the study or within 5 half-lives of the investigational drug (whichever is the longer)

Primary Endpoints:
Stimulated C-peptide and insulin (see below)
HbA1c
Fasting plasma glucose (FPG)

Secondary Endpoints:
Insulin requirement
Serum cytokines levels, CRP
Insulin secretion and Insulin-sensitivity index derived from an OGTT with insulin and glucose measurements.
In a subgroup of patients, insulin-sensitivity assessed by clamp techniques as well as by muscle and fat biopsies.

Patient Evaluation
Patients will be evaluated as follows:
Physical examination including Body Mass Index, Waist to Hip Ratio, blood pressure (standing and supine), heart rate
Blood samples for determination of HbA1c, lipid profile including free fatty acids, HDL- and LDL-cholesterol, IL-1β, IL-1Ra, IL-6, TNFα, CRP, sodium, potassium, creatinine, AST, ALT, and hematogramm.
24 h urine collection for albuminuria and creatinine clearance (only baseline and end of study).
Ophthalmologic examination including strereoscopic fundus photography (only baseline and end of study)
Standard oral glucose-tolerance-test (OGTT) with measurement of plasma blood glucose, insulin and C-peptide at 0, 30, 60, 90 and 120 min. At 120 min, 0.3 g/kg glucose+0.5 mg glucagon+5 g arginine will be injected intravenously followed by measurement of plasma blood glucose and insulin at 0, 3, 6, 9 and 12 min.
Weekly full blood glucose profile performed at home by the patient.
Euglycemic-hyperinsulinemic clamp and biopsies: a subset of 40 patients (20 IL-1Ra- and 20 placebo-treated) will undergo an euglycemic-hyperinsulinemic clamp as well as a muscle and fat biopsy. This technique is routinely used in the group of A. Vaag at the SDC (63-65). M. Faulenbach will learn the technique at the SDC and introduce it at the USZ. Polyethylene catheters will be placed in the antecubital vein for infusion and in the contralateral dorsal hand or antecubital vein for blood sampling. This "sampling" hand will be placed in a heated Plexiglas box to ensure arterialization of the venous blood sample. After an initial 40-min basal period, a primed-continuous insulin infusion (40 mU·m$^-$$_2$·min$^{-1}$) will be initiated and continued for 3 h. Basal and insulin stimulated steady state periods will be defined as the last 30 min of the 40 min basal state period and the last 30 min period of the 3 h clamp period. A variable infusion of glucose (180 g/l) will maintain euglycaemia during insulin infusion. Plasma glucose concentration will be monitored every 5 to 10 min during the basal and clamp periods using an automated glucose oxidation method. Blood samples will be drawn for measurements of insulin every 10 to 30 min during the basal and clamp steady state periods. Needle biopsies will be obtained in the basal state (time 0 min) from the vastus lateralis muscle and from the subcutaneous fat of the same region as well as from the abdominal region. The biopsies will be immediately frozen in liquid nitrogen and stored at −80° C. until analyzed for expression of cytokines (e.g. TNFα, IL-1α and β, IL-1Ra, IL-6, adiponectin and leptin) as well as for other genes and proteins of potential importance for insulin action.

The patients will be instructed to abstain from strenuous physical activity for 24 h and to fast for 9-10 h before both tests (OGTT and clamp studies). They should receive an injection of the study medication on study days but not other antidiabetic medications. The clamp will follow the OGTT, with a separation of 2 to 7 days. Study medication will be continued until the end of all assessments.

Basic Medication:

Any change of patients' current therapy during the study should be avoided.

Study Medication:

Anakinra (Kineret©) is the recombinant, nonglycosylated form of the IL-1Ra with an N-terminal methionine and is produced by Amgen. By competitively binding to the interleukin-1 type I receptor, anakinra inhibits the activity of IL-1. FDA approval for a 100 mg dose via subcutaneous injection for 6 months occurred in November 2001. Anakinra has a half-life of 4-6 hours and a maximum plasma concentration at 3-7 hours after subcutaneous administration of 1-2 mg/kg.

Anakinra will be given every 24 h in a single morning dose of 100 mg. Anakinra or placebo (saline) will be injected subcutaneously into the skin of the abdomen or upper thighs. The study nurse will instruct the patients how to perform the injections by themselves. One physician will always be available throughout 24 h for health or any other problems.

Ethical Considerations:

Adverse Reactions

Injection site reactions, characterized by erythema, ecchymosis, pruritus, inflammation, pain, and swelling, are the most commonly reported adverse effects of subcutaneous treatment in rheumatoid arthritis patients. Reactions were usually mild and transient, resolving within several weeks; however, discontinuation of treatment has been required in up to 5% of patients. In clinical trials of rheumatoid arthritis, neutropenia with absolute neutrophil count $1 \times 10^9/l$ or less developed in 0.3% of patients who received IL-1Ra in placebo-controlled trials. Infections occurred in 40% of patients who received IL-1Ra and 35% of patients who received placebo (n. s.). Serious infections occurred in 1.8% of the IL-1Ra group and 0.6% of the placebo group during a 6-month period (n. s.). Serious infections were primarily bacterial (cellulitis, pneumonia, bone and joint infections) rather than opportunistic, fungal, or viral.

Invasive Investigations (Clamp and Biopsies)

The euglycemic-hyperinsulinemic clamp is the gold standard technique to assess insulin sensitivity. All the necessary catheters involve only peripheral veins. Blood glucose will be monitored every 5 to 10 min, which should be sufficient to avoid hypoglycemia.

A muscle and fat biopsy will give unique insight into the effect of IL-1Ra on insulin-sensitive tissues. Local anesthesia will avoid any significant discomfort. The size of the samples will be maximum $0.5\ cm^3$.

Injections of Study Medication

Most of the participating patients will eventually have to inject insulin. Therefore, the burden to learn and get used to auto-subcutaneous injection will be beneficial for most of them in the long-term.

Delay of Instituting Insulin Therapy Until 13 Weeks

Since severely hyperglycemic patients are excluded from the study, a possible delay of 13 weeks until they start using insulin, should not significantly increase the risk of developing long-term complications of diabetes.

Breaking of Criteria

Patients have the right to withdraw at any given time from the study without giving a reason. The study doctor can interrupt or end the therapy if any side effects arise or an unexpected course of the therapy is detected, or if it would be in the interest of the patient. In this situation, the study doctor decides on the following therapeutic measures. Withdrawal from the study will not affect further care.

Informed-Consent

A written informed-consent form will be obtained from each patient.

Statistics

Based on a power calculation including an expected 30% change in stimulated insulin, an SD of 50%, a power $(1-\beta)$ of 80% and a significance of $\alpha=0.05$, it is estimated that a sample size of 72 (placebo:IL-1Ra 1:1) will be required.

Student's two tailed t-test will be used for comparison of means. Multiple measurements obtained over time will be analyzed by one-way-analysis of variance (ANOVA) for repeated measures. Matched-pairs (comparison of baseline measurements and follow-up) will be tested by the Wilcoxon test.

Blinding and randomization will be performed by the Kantonsapotheke, Zurich.

Anticipated Conclusion

Assuming that glucotoxicity will be completely blocked by IL-1Ra, the following improvements can be expected in IL-1Ra treated patients as compared to baseline or placebo-treated patients:

60% (or higher) increase in stimulated C-peptide and insulin levels.

Improvement of HbA1c: depending on baseline HbA1c, a decrease of HbA1c of 1% (baseline 8%) to 4% (baseline 12%).

Fasting plasma glucose (FPG): depending on baseline FPG, a decrease of FPG by 13% (baseline 8 mM glucose) to 27% (baseline 15 mM glucose).

No insulin requirement in the IL-1Ra-treated group versus 0.8 IU/Kg insulin in the placebo-treated.

60% (or higher) increase in insulin-sensitivity.

Normalisation of serum cytokines and CRP levels.

Further Study of Role of IL-1Ra in Type 2 Diabetes

The invention is further supported by the result of the following study of the molecular link between obesity and type 2 diabetes, in particular the role of IL-1Ra.

Obesity is associated with an increased risk of diabetes, but the mechanisms of this progression are unclear. Most obese people are insulin resistant and have to adapt by increasing insulin secretion. The β-cell mass itself is the major factor in the amount of insulin that can be secreted and β-cell mass increases during obesity (66;62). In individuals who lose the ability to produce sufficient quantities of insulin to maintain normoglycemia in the face of insulin resistance, type 2 diabetes mellitus manifests (67). Increasing evidence suggests that a progressive decrease in β-cell mass, and not only β-cell function, contributes to this (62;68;69). The deficit of β-cell mass in the pathophysiology of type 2 diabetes seems to be due to increased β-cell apoptosis (62;70). Possible mediators of the process of β-cell destruction are increased serum concentrations of cell nutrients. Indeed, increased free fatty acid (FFA) levels per se are known to be toxic for β-cells, leading to the concept of lipotoxicity (12;71-75). However, not all obese individuals or pre-type 2 diabetes patients exhibit dyslipidemia. Thus, lipotoxicity may play an important role in the process of β-cell destruction but probably does not act alone. Elevated glucose concentrations induce β-cell apoptosis in cultured islets from diabetes-prone *Psammomys obesus*, an animal model of type 2 diabetes (70), in human islets (9-10;76-77) and at higher concentrations in rodent islets (11-12). In human islets, glucose-induced β-cell apoptosis and dysfunction are mediated by β-cell production and secretion of IL-1β (76). Probably already in the pre-type 2 diabetic stage, insulin resistance diminishes glucose uptake, resulting in transient post-prandial hyperglycemic excursions, supporting the glucotoxicity hypothesis (3-7;35;78-80). This transient hyperglycemia could act on the β-cells even before diabetes manifests itself or at the very early stages of the disease, but it is unclear whether this is sufficient to cause progression from obesity to diabetes.

Leptin is expressed primarily in the adipose tissue and therefore represents the most obvious exponent of the adipocyte (81). β-cells express leptin receptors, leptin inhibits insulin secretion in vivo and in vitro (82-85). In rodent islets, leptin induces β-cell proliferation and protects from FFA-induced β-cell apoptosis (86-89). However, the effect of leptin on human β-cell apoptosis is not known. This is of particular interest, because human β-cells often respond differently than rodent islets with respect to stimuli of apoptosis. For example, increasing ambient glucose concentrations from physiologic 5.5 mM to 11.1 mM decreases the rate of β-cell apoptosis in rodents islets, whereas it induces apoptosis in human islets (9;11).

Interleukin-1 receptor antagonist (IL-1Ra) is an anti-inflammatory cytokine and naturally occurring antagonist of IL-1α and β (90;91). Similarly to IL-1β, IL-1Ra binds to type 1 IL-1 receptor but it lacks a second binding domain and therefore does not recruit the IL-1 receptor accessory protein, the second chain of the receptor complex. Three forms of IL-1Ra have been described, two of them are intracellular proteins (icIL-1Ra I and II) and one is secreted. The function of icIL-1Ra is not known (93). Exogenous recombinant human (rh) IL-1Ra protects cultured human islets from glucose-induced, IL-1β-mediated, β-cell apoptosis and improves β-cell function (76). Interestingly, leptin induces secretion of IL-1Ra in monocytes (93). However, expression and regulation of IL-1Ra in human islets have not been investigated.

Therefore, IL-1Ra in human pancreatic β-cells of non-diabetic and diabetic patients was studied and its regulation by leptin was identified. Effects of leptin on IL-1 production and on human β-cell survival and function, partly mediated by changes in IL-1Ra expression, were also explored.

Methods

Islet isolation and cell culture. Islets were isolated from pancreases of ten organ donors at the Department of Surgery, University of Geneva Medical Center, as described (32-34). The islet purity was >95%, as judged by dithizone staining (if this degree of purity was not primarily achieved by routine isolation, islets were handpicked). The donors, aged 40-65 years, were heart-beating cadaver organ donors, and none had a previous history of diabetes or metabolic disorders. For long-term in vitro studies, the islets were cultured on extracellular matrix-coated plates derived from bovine corneal endothelial cells (Novamed Ltd., Jerusalem, Israel), allowing the cells to attach to the dishes and spread, preserving their functional integrity (7;35). Islets were cultured in CMRL 1066 medium containing 100 U/ml penicillin, 100 μg/ml streptomycin and 10% fetal calf serum (Invitrogen Corporation, Paisley, U.K.), hereafter referred to as culture medium. Two days after plating, when most islets were attached and began to flatten, the medium was changed to culture medium containing 5.5, 11.1 or 33.3 mM glucose. In some experiments, islets were additionally cultured with 5, 10 or 500 nM rh leptin (PeproTech, London, UK), 500 ng/ml rh IL-1Ra (R&D Systems Inc., Minneapolis, Minn.) or 50 nM small interfering RNA (siRNA) as described below.

Human blood monocytes were isolated as described previously (37), cultured in RPMI 1640 (Invitrogen) containing 100 U/ml penicillin, 100 μg/ml streptomycin and 10% fetal calf serum and exposed to 10 or 500 nM leptin.

RNA interference. RNAs of 21 nucleotides, designed to target human IL-1Ra (5'AUCUGCAGAGGCCUCCG-CAtt3'/5'UGCGGAGGCCUCUGCAGAUtt3') and scrambled siRNA were synthesized by Ambion (Austin, Tex.). siRNAs were transfected using SiPortAmine™ according to the manufacturer's instructions (Ambion).

Detection of IL-1Ra and IL-1β expressing cells. Pancreases from routine necropsies were immersion-fixed in formalin, followed by paraffin embedding. In parallel, isolated human were cultured in a suspension for 48 hours and exposed to 10 nM leptin or 33.3 mM glucose, islets were fixed in Bouin solution for 15 min, resuspended in 40 μl of 2% melted agarose in PBS (40° C.), followed by rapid centrifugation and paraffin embedding. Sections were deparaffinized, rehydrated and then incubated in methanol for 4 min. Human islets cultured on extracellular matrix for 4 days were washed in PBS, fixed in 4% paraformaldehyde (30 min, room temperature) followed by permeabilization with 0.5% triton X-100 (4 min, room temperature). Pancreas and islet sections and cultured cells were double-labeled for IL-1Ra or IL-1β and insulin, CD68, glucagon or somatostatin by 1 h of exposure to 10% bovine serum albumin followed by incubation (1 h, 37° C.) with biotinylated goat anti-IL-1Ra or mouse anti-IL-1β antibodies (R&D Systems Inc.). Detection was performed using cy3-(Jackson, ImMunoResearch Laboratories, West Grove, Pa.) or cy2-(Transduction Lab., Lexington, Ky.) conjugated streptavidin. Subsequently, specimens were incubated for 30 min at 37° C. with guinea-pig (Dako, Carpinteria, Calif.) or mouse (Sigma) anti-insulin, rabbit anti-somatostatin (Dako), rabbit anti-glucagon (Dako) or mouse anti-CD68 (Biosource, Nivelles, Belgium) antibodies, followed by a 30 min incubation with FITC-conjugated rabbit anti-guinea pig (Dako), cy3-conjugated donkey anti-mouse, cy3-conjugated donkey anti-rabbit or cy2-conjugated donkey anti-mouse antibodies (Jackson).

Electron microscopy. Human islets maintained in culture medium in nonadherent plastic dishes were fixed in a solution containing freshly made 2.5% paraformaldehyde, 0.1% glutardialdehyde and 0.01% picric acid for about 4 h at room temperature. Thereafter, specimens were dehydrated in an ascending series of ethanol and routinely embedded in LR White (Polysciences, Warrington, Pa., USA). Ultrathin sections were treated with 50 mM gelatine in 10 ml PBS containing 0.2 g BSA and rinsed in PBS. Sections were incubated with guinea-pig anti-porcine insulin (code: A564; 1:400; Dako) overnight at room temperature, washed in PBS, followed by anti guinea pig IgG conjugated with a gold-5 nm complex (1:50, Amersham Int., Little Chalfont, UK) for 30 min. Thereafter, sections were rinsed in double-distilled water, air dried, and incubated with the biotinylated goat anti-IL-1Ra antibody as described above, washed in PBS followed by incubation with a streptavidin-gold-5 nm complex (1:50, Amersham) for 1 h at room temperature. Sections were counterstained with uranyl acetate for 4 min and examined and photographed with a Philips EM 420 electron microscope.

Western blot analysis. Human islets were maintained in culture medium in nonadherent plastic dishes. One day after isolation, the medium was changed and groups of 200 islets were incubated in culture medium containing 5.5 glucose with or without 10 or 500 nM leptin or 50 nM siRNA. At the end of the incubations, islets were washed in PBS, suspended in 40 µl sample buffer containing 125 mM Tris-HCl (pH 6.8), 4% SDS, 10% glycerol, 0.3% bromphenol blue, 1.8% β-mercaptoethanol and boiled for 5 min. Equivalent amounts of each treatment group were run on 15% SDS polyacrylamide gels. Proteins were electrically transferred to nitrocellulose filters and incubated with biotinylated goat anti-IL-1Ra, mouse anti-caspase 3 (which binds to both, procaspase-3 and activated caspase-3; Pharmingen, San Diego, Calif.), or mouse anti-actin (C-2; Santa Cruz Biotechnology Inc., Santa Cruz, Calif.) antibodies, followed by incubation with horseradish-peroxidase-linked anti-mouse (Santa Cruz Biotechnology Inc.) or streptavidin (Jackson). The emitted light was captured on X-ray film after adding Lumi-Light Western Blotting Substrate (Roche, Basel, Switzerland). As a marker, Kaleidoscope Prestained Standards (Bio Rad, Laboratories inc., Hercules, Calif.) was run in parallel. Between incubations, nitrocellulose membranes were stripped for 30 min at 50° C. in 40 ml of a solution containing 280 µl β-mercaptoethanol, 5 ml 0.5 M Tris-HCl (pH 6.8) and 10% SDS, and then washed for 1 h in Tris-buffered saline containing 0.10/0 Tween-20.

RNA extraction and RT-PCR. Islets were cultured in a suspension as described above. Total RNA was extracted using Rneasy mini kit (Qiagen, Basel, Switzerland) and RT-PCR was performed using the Superscript™ II Rnase H-Reverse transcriptase kIT and oligo (dT) (7) (Life technologies, Gaithersburg, Md., USA) according to the instructions from the manufacturers. The following primers were used: 5'ACTGAGGACCAGCCATTGAG3'(SEQ ID. NO. 1)/5'AGGTG-GAATGAGGGAGGAAG3' (human IL-1Ra) (SEQ ID.NO. 2) and 5'AAGCTGATGGCCCTAAACAG3'(SEQ ID. NO. 3)/5'AGGTGCATCGTGCACATAAG3' (human IL-1β) (SEQ ID. NO. 4). PCR conditions were: denaturation for 30 seconds at 94° C., annealing for 30 seconds at 60° C., and elongation for 30 seconds at 72° C., followed for real time PCR by quantification for 5 seconds at 82° C.; repetition for 40 cycles. Saturation of PCR product occurred between 19 and 33 cycles. The size of the PCR amplification product was 250 bp. For quantitative analysis, we used the LightCycler quantitative PCR system (Roche) and performed quantitative PCR with a commercial kit (LightCycler-DNA Master SYBR Green I; Roche). The amounts of IL-1Ra mRNA were standardized against α-Tubulin (5'AGAGTCGCGCTGTAA-GAAGC3'(SEQ ID. NO. 5)/5'TGGTCTTGTCACTTG-GCATC3' (SEQ ID. NO. 6)) and GAPDH (5'AACAGCGACACCCACTCCTC3'(SEQ ID. NO. 7)/5'GGAGGGGAGATTCAGTGTGGT3'(SEQ ID. NO. 8)) with similar results.

β-cell apoptosis. The free 3'-OH strand breaks resulting from DNA degradation were detected using the terminal deoxynucleotidyl transferase-mediated dUTP nick-end labeling (TUNEL) technique as described in detail (70;76; 77). Thereafter, islets were incubated with guinea pig anti-insulin antibody as above, followed by detection using the streptavidin-biotin-peroxidase complex (Zymed Laboratories Inc., South San Francisco, Calif., USA). In parallel to the TUNEL reaction, apoptosis was confirmed by detection of caspase 3 activation as described above (Western blot analysis).

Cytokine release. Cytokine release was evaluated in the culture medium collected before the termination of each experiment using human IL-1β and IL-1Ra ELISA kits (R&D Systems Inc.).

Insulin release and content. To determine acute insulin release in response to glucose stimulation, islets were washed in Kreb's ringer bicarbonate buffer (KRB-Hepes, pH 7.4: 4.8 mM KCl, 134 mM NaCl, 5 mM NaHCO$_3$, 1.2 mM MgSO$_4$, 1.2 mM KH$_2$PO$_4$, 1 mM CaCl$_2$, 0.5% BSA, 10 mM HEPES) containing 3.3 mM glucose and pre-incubated for 30 min in the same buffer. The KRB was then discarded and replaced by fresh buffer containing 3.3 mM glucose for 1 h for basal secretion, followed by an additional 1 h of incubation in KRB containing 16.7 mM glucose. Supernatants were collected and frozen for insulin assays. Thereafter, islets were washed with PBS and extracted with 0.18 N HCl in 70% ethanol for 24 h at 4° C. The acid-ethanol extracts were collected for determination of insulin content. Insulin was determined by a human insulin RIA kit (CIS bio international, Gif-Sur-Yvette, France).

Evaluation and statistical analysis. Samples were evaluated in a randomized manner by a single investigator (K.M.) who was blinded to the treatment conditions. Care was taken to score islets of similar size. Some larger islets did not completely spread and were several cells thick. Such larger islets were excluded because a monolayer is a prerequisite for single cell evaluation. The mean surface of the evaluated islet-monolayers was determined previously in islets cultured at 5.5 and 33.3 mM glucose, respectively, and found to be similar (76;77). Thus, the exclusion of larger islets occurred to a similar extent in each dish independently of the treatment. Data were analyzed by student's t test or by analysis of variance with a Bonferroni correction for multiple group comparisons.

Results

IL-1Ra is expressed by human pancreatic β-cells and downregulated in type 2 diabetic patients. Immunodetection of human pancreatic sections from non-diabetic patients revealed the presence of IL-1Ra localized in the β-cells (FIGS. 7A & B). Additionally, some non-β-cells expressed IL-1Ra and were identified as resident macrophages (CD68 positive; FIGS. 7E & F). No specific staining for IL-1Ra was observed in a and 5 cells, as assessed by double immunostaining with anti-IL-1Ra and anti-glucagon or anti-somatostatin antibodies, respectively. IL-1Ra was also undetectable in the exocrine tissue. Expression of IL-1Ra by the β-cell itself was confirmed by electron microscopy of sections from isolated human islets (FIG. 7G). Next, expression of IL-1Ra in sections of pancreases from six poorly controlled type 2 diabetic patients was studied, all with documented fasting blood glucose >8 mM (Table 2). In all pancreases, IL-1Ra protein expression was decreased as compared to the no diabetic controls (for representative images see FIGS. 7C & D).

TABLE 2

|  | No | age | sex | glucose (mM) | diagnosis |
| --- | --- | --- | --- | --- | --- |
| diabetic | 1 | 90 | f | 8.9 | COPD |
|  | 2 | 87 | f | 14.3 | Lymphoma |
|  | 3 | 74 | f | 21.9 | MI |
|  | 4 | 71 | m | 13.4 | pulmonary embolism |
|  | 5 | 69 | m | 10.0 | lung cancer |
|  | 6 | 65 | f | 10.3 | AP |

TABLE 2-continued

|  | No | age | sex | glucose (mM) | diagnosis |
|---|---|---|---|---|---|
| control | 7 | 77 | f | 5.0 | Hypertension |
|  | 8 | 54 | m | 5.0 | Lymphoma |
|  | 9 | 81 | m | 5.5 | CHF |
|  | 10 | 68 | f | 6.0 | Mammacarcinoma |
|  | 11 | 78 | f | 6.7 | MI |
|  | 12 | 31 | m | 5.0 | Melanoma |

Age, sex, plasma glucose concentration and diagnosis of type 2 diabetic and control patients.

Figure 1:
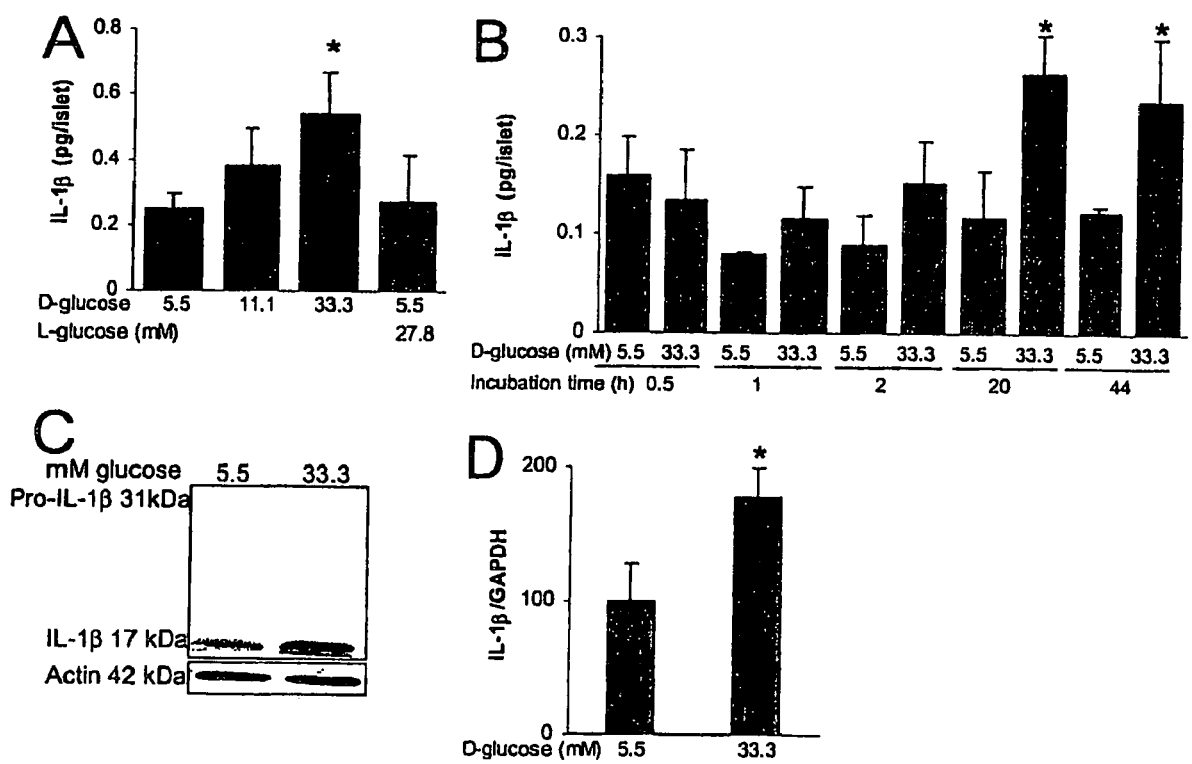
FIG. 1—Glucose induces IL-1β expression and release in human islets.

Leptin decreases β-cell production of IL-1Ra and induces IL-1β release in human islets. The hypothesis that high concentration of glucose was responsible for the in vivo regulation of IL-1Ra expression was investigated in vitro in primary culture of human islets. Exposure of islets to 33.3 mM glucose for 48 h did neither affect IL-1Ra protein expression (FIG. 8A-1 to A-4) nor IL-1Ra release or mRNA expression (FIG. 9A), as compared to controls at 5.5 mM glucose. Because leptin regulates IL-1Ra secretion in monocytes (93), we then postulated that it may be a regulator of IL-1Ra in β-cells. Exposure of cultured human islets to 10 nM leptin for 48 hours decreased IL-1Ra expression in most β-cells, as determined by double immunostaining (FIGS. 8A-5 & A-6). Western blot analysis of IL-1Ra in human islets revealed that leptin decreased IL-1Ra already after a 15-hour exposure (FIG. 8B). Interestingly, IL-1Ra released into the culture medium and IL-1Ra mRNA were increased after short-term exposure to 10 to 500 nM leptin for 15 hours, but longer exposure for 48 hours resulted in a marked decrease (FIGS. 8C-1 & C-2). A similar dual effect was observed in peripheral blood monocytes that were used as control (FIGS. 8C-3 & C-4).

IL-1Ra action depends on IL-1β, which is why also the regulation of IL-1β by leptin was studied. Similarly to the regulation of IL-1Ra, exposure of human islets to leptin for 15 hours increased IL-1β release into culture medium (FIG. 8D-1). In contrast to the leptin-induced decrease of IL-1Ra release after 48 hour, IL-1β release remained increased after a 48 hour exposure. Moreover, exposure of peripheral blood monocytes to leptin for 15 hours increased IL-1β release, whereas prolonged exposure for 48 hours did not significantly affect IL-1β release (FIG. 8D-2). Quantitative RT-PCR measurements revealed that IL-1β RNA expression of islets was not significantly changed by leptin. Nevertheless, exposure of cultured human islets to 10 nM leptin for 48 hours induced IL-1β expression in TUNEL-positive β-cells, as determined by triple-immunostaining of islets with anti-IL-1β and anti-insulin antibodies and by the TUNEL assay (FIG. 8E).

Endogenously produced IL-1Ra is a survival factor of β-cells and preserves β-cell function. We next studied the functional role of IL-1Ra in human β-cells by means of siRNA. Two days after exposure of human islets to siRNA to IL-1Ra (siIL-1Ra), endogenous IL-1Ra RNA expression decreased by 69.4±6.5% as compared to islets incubated at 5.5 mM glucose alone, whereas scrambled siRNA had no such effect (FIG. 9A). Antagonization of IL-1Ra was similar at low (5.5 mM) and high (33.3 mM) glucose concentrations (FIG. 9A). SiIL-1Ra dramatically decreased IL-1Ra protein expression inducing an apoptotic process demonstrated by caspase 3 activation (FIG. 9B) and β-cell DNA fragmentation (TUNEL-positive nuclei, FIGS. 9C & D). Addition of exogenous rhIL-1Ra prevented the effect of siIL-1Ra on DNA fragmentation, proving the specificity of the RNA interference (FIGS. 9C & D). Exposure of cultured human islets to elevated glucose concentrations increased the number of β-cells displaying DNA fragmentation (FIG. 9D). This glucose effect was enhanced by co-incubation with siIL-1Ra, whereas exogenous rhIL-1Ra protected the β-cells from apoptosis induced by 33.3 mM glucose alone and partially from 33.3 mM glucose and siIL-1Ra.

Next, the role of endogenous IL-1Ra on β-cell function was evaluated. Antagonizing IL1-Ra by siRNA dramatically decreased the ratio of basal to acute glucose-stimulated insulin release of human islets maintained at 5.5 mM glucose (FIG. 9E-1). Co-incubation with exogenous rh IL-1Ra restored glucose stimulation. Chronic exposure of human islets to 11.1 mM glucose severely blunted acute glucose-stimulated insulin release, which was totally lost in the presence of siIL-1Ra at 11.1 or 33.3 mM glucose and by 33.3 mM alone. Exogenous rh IL-1Ra partially prevented those effects. Insulin contents of islets exposed to siIL-1Ra and/or high glucose concentrations were decreased compared to control (5.5 mM glucose) and partially restored by rh IL-1Ra (FIG. 9E-2)

Leptin induces β-cell apoptosis and impairs β-cell function via IL-1β-signaling. Exposure of cultured human islets to 10 nM leptin for 4 days increased the number of TUNEL-positive β-cells (FIG. 10A). Moreover, leptin enhanced 33.3 mM glucose-induced apoptosis (FIG. 10A). To demonstrate an apoptotic process, in parallel to the TUNEL assay, caspase 3 activation was detected. Exposure of human islets to leptin for 15 hours did not change baseline cleaved caspase 3 level, but an increase became apparent after 48 hours (FIG. 10B). Moreover, exposure of leptin for 4 days decreased chronic insulin secretion during the culture period by 41.65% (p<0.01), impaired glucose-stimulated insulin secretion and decreased insulin content at 5.5 mM glucose, an effect which was additive to the deleterious effect of high glucose (FIG. 10C). Finally, to show that leptin-induced DNA fragmentation, impaired β-cell function and decreased insulin content are mediated by the dysbalance of IL-1β and IL-1Ra, human islets were co-incubated with leptin and exogenous rh IL-1Ra. In human islets exposed to leptin, addition of rh IL-1Ra prevented leptin-induced β-cell apoptosis and restored β-cell function and insulin content (FIG. 10D).

Chronically elevated blood glucose levels impair the function of β-cells in the pancreas (3-7;35;78-80). When studying the underlying mechanisms, we have previously observed that exposure of cultured islets to elevated glucose levels leads to β-cell production and release of IL-1β, followed by impaired β-cell function and death (76). The present data show that the IL-1β pathway is not only involved in glucotoxicity but is also a mediator of obesity-associated diabetes. Indeed, leptin, the protein encoded by the ob gene, decreased β-cell expression of IL-1Ra. In parallel, exposure of human islets to leptin induced IL-1β release. Leptin-induced changes in the IL-1β/IL-1Ra ratio, impaired β-cell function and enhanced β-cell apoptosis. The deleterious effects of leptin can be alleviated by supplementation of exogenous IL-1Ra in a similar way as it can palliate glucotoxicity.

To the best of our knowledge, this is the first study which shows expression of IL-1Ra by the β-cells. This is particularly intriguing in the context of an endocrine organ not primarily belonging to the immune system. In addition to the previous findings which show β-cell expression of IL-1β (76;50), the present observation provides further evidence of local inflammatory mediators in the pathophysiology of diabetes (94).

Antagonizing endogenous β-cell-IL-1Ra by siRNA led to impaired β-cell function and apoptosis. This is not an unspecific effect of siRNA, since scrambled siRNA was not toxic. It is likely that a certain amount of IL-1Ra is necessary for the survival of cultured human β-cells. Possibly, IL-1β, which is present in the supernatant of untreated cultured human islets (76) is ineffective as long as IL-1Ra is expressed and becomes deleterious as soon as the balance changes in its favor. In vivo, it is conceivable that IL-1Ra protects the β-cells from other sources of IL-1β, e.g. the innate immune system (94), and that the β-cells become particularly vulnerable if leptin decreases its expression.

The cellular source of leptin-induced IL-1β of the islet is not clear. Triple immunostaining for IL-1β, insulin and the TUNEL assay of islets exposed to leptin uncovered only TUNEL-positive β-cells producing IL-1β. Those cells are probably not the unique source of leptin-induced IL-1β. Indeed, rhIL-1Ra blocked leptin-induced apoptosis. Therefore, part of leptin-induced IL-1β precedes the apoptotic process. Alternatively, islet resident macrophages may well contribute to leptin production, since leptin induces the secretion of IL-1β in peripheral blood monocytes, as previously shown (93) and confirmed in the present study.

In normal individuals, the endocrine pancreas responds to an increased insulin demand by increasing its function and mass (62;66;95). The failure to adapt in diabetes may be partly explained by the deleterious effects of chronic exposure to leptin and to elevated glucose excursions. Intra-islet production of IL-1β and decreased IL-1Ra expression appear as a final common pathway responsible for impaired β-cell function and apoptosis. Therefore, therapeutic approaches designed to block this pathway may block leptin- and glucotoxicity, preventing a progressive decline in β-cell mass and restoring β-cell function. IL-1Ra appears to be a suitable therapeutic agent for this purpose.

REFERENCES

1. Unger, R. H. and Grundy, S. 1985. Hyperglycaemia as an inducer as well as a consequence of impaired islet cell function and insulin resistance: implications for the management of diabetes. *Diabetologia* 28:119-121.
2. Kaiser, N., Corcos, A. P., Sarel, I., and Cerasi, E. 1991. Monolayer culture of adult rat pancreatic islets on extracellular matrix: modulation of β-cell function by chronic exposure to high glucose. *Endocrinology* 129:2067-2076.
3. Leahy, J. L., Cooper, H. E., Deal, D. A., and Weir, G. C. 1986. Chronic hyperglycemia is associated with impaired glucose influence on insulin secretion. A study in normal rats using chronic in vivo glucose infusions. *J. Clin. Invest* 77:908-915.
4. Robertson, R. P. 1989. Type II diabetes, glucose "nonsense," and islet desensitization. *Diabetes* 38:1501-1505.
5. Rossetti, L., Giaccari, A., and DeFronzo, R. A. 1990. Glucose toxicity. *Diabetes Care* 13:610-630.
6. Eizirik, D. L., Korbutt, G. S., and Hellerstrom, C. 1992. Prolonged exposure of human pancreatic islets to high glucose concentrations in vitro impairs the beta-cell function. *J Clin Invest* 90:1263-1268.
7. Marshak, S., Leibowitz, G., Bertuzzi, F., Socci, C., Kaiser, N., Gross, D. J., Cerasi, E., and Melloul, D. 1999. Impaired beta-cell functions induced by chronic exposure of cultured human pancreatic islets to high glucose. *Diabetes* 48:1230-1236.
8. Donath, M. Y., Gross, D. J., Cerasi, E., and Kaiser, N. 1999. Hyperglycemia-induced beta-cell apoptosis in pancreatic islets of *Psammomys obesus* during development of diabetes. *Diabetes* 48:738-744.
9. Maedler, K., Spinas, G. A., Lehmann, R., Sergeev, P., Weber, M., Fontana, A., Kaiser, N., and Donath, M. Y. 2001. Glucose induces b-cell apoptosis via upregulation of the Fas-receptor in human islets. *Diabetes* 50:1683-1690.
10. Federici, M., Hribal, M., Perego, L., Ranalli, M., Caradonna, Z., Perego, C., Usellini, L., Nano, R., Bonini, P., Bertuzzi, F. et al. 2001. High glucose causes apoptosis in cultured human pancreatic islets of Langerhans: a potential role for regulation of specific Bcl family genes toward an apoptotic cell death program. *Diabetes* 50:1290-1301.
11. Efanova, I. B., Zaitsev, S. V., Zhivotovsky, B., Kohler, M., Efendic, S., Orrenius, S., and Berggren, P. O. 1998. Glucose and tolbutamide induce apoptosis in pancreatic beta-cells. A process dependent on intracellular Ca2+ concentration. *J Biol Chem* 273:33501-33507.
12. Maedler, K., Spinas, G. A., Dyntar, D., Moritz, W., Kaiser, N., and Donath, M. Y. 2001. Distinct effects of saturated and monounsaturated fatty acids on beta-cell turnover and function. *Diabetes* 50:69-76.
13. Tajiri, Y., Moller, C., and Grill, V. 1997. Long-term effects of aminoguanidine on insulin release and biosynthesis: evidence that the formation of advanced glycosylation end products inhibits B cell function. *Endocrinology* 138:273-280.
14. Robertson, R. P., Zhang, H. J., Pyzdrowski, K. L., and Walseth, T. F. 1992. Preservation of insulin mRNA levels and insulin secretion in HIT cells by avoidance of chronic exposure to high glucose concentrations. *J. Clin. Invest* 90:320-325.
15. Robertson, R. P., Olson, L. K., and Zhang, H. J. 1994. Differentiating glucose toxicity from glucose desensitization: a new message from the insulin gene. *Diabetes* 43:1085-1089.
16. Mandrup-Poulsen, T. 1996. The role of interleukin-1 in the pathogenesis of IDDM. *Diabetologia* 39:1005-1029.
17. Mandrup-Poulsen, T., Bendtzen, K., Nielsen, J. H., Bendixen, G., and Nerup, J. 1985. Cytokines cause functional and structural damage to isolated islets of Langerhans. *Allergy* 40:424-429.
18. Bendtzen, K., Mandrup-Poulsen, T., Nerup, J., Nielsen, J. H., Dinarello, C. A., and Svenson, M. 1986. Cytotoxicity of human pI 7 interleukin-1 for pancreatic islets of Langerhans. *Science* 232:1545-1547.
19. Spinas, G. A., Hansen, B. S., Linde, S., Kastern, W., Molvig, J., Mandrup-Poulsen, T., Dinarello, C. A., Nielsen, J. H., and Nerup, J. 1987.—Interleukin 1 dose-dependently affects the biosynthesis of (pro)insulin in isolated rat islets of Langerhans. *Diabetologia* 30:474-480.
20. Mandrup-Poulsen, T., Bendtzen, K., Nerup, J., Dinarello, C. A., Svenson, M., and Nielsen, J. H. 1986. Affinity-purified human interleukin I is cytotoxic to isolated islets of Langerhans. *Diabetologia* 29:63-67.
21. Spinas, G. A., Mandrup-Poulsen, T., Molvig, J., Baek, L., Bendtzen, K., Dinarello, C. A., and Nerup, J. 1986. Low concentrations of interleukin-1 stimulate and high concentrations inhibit insulin release from isolated rat islets of Langerhans. *Acta Endocrinol. (Copenh)* 113:551-558.
22. Yamada, K., Takane-Gyotoku, N., Yuan, X., Ichikawa, F., Inada, C., and Nonaka, K. 1996. Mouse islet cell lysis mediated by interleukin-1-induced Fas. *Diabetologia* 39:1306-1312.
23. Corbett, J. A., Lancaster, J. R., Jr., Sweetland, M. A., and McDaniel, M. L. 1991. Interleukin-1 beta-induced formation of EPR-detectable iron-nitrosyl complexes in islets of Langerhans. Role of nitric oxide in interleukin-1 beta-induced inhibition of insulin secretion. *J. Biol. Chem.* 266: 21351-21354.

24. Giannoukakis, N., Rudert, W. A., Ghivizzani, S. C., Gambotto, A., Ricordi, C., Trucco, M., and Robbins, P. D. 1999. Adenoviral gene transfer of the interleukin-1 receptor antagonist protein to human islets prevents IL-1beta-induced beta-cell impairment and activation of islet cell apoptosis in vitro. *Diabetes* 48:1730-1736.

25. Giannoukakis, N., Mi, Z., Rudert, W. A., Gambotto, A., Trucco, M., and Robbins, P. 2000. Prevention of beta cell dysfunction and apoptosis activation in human islets by adenoviral gene transfer of the insulin-like growth factor I. *Gene Ther.* 7:2015-2022.

26. Loweth, A. C., Williams, G. T., James, R. F., Scarpello, J. H., and Morgan, N. G. 1998. Human islets of Langerhans express Fas ligand and undergo apoptosis in response to interleukin-1beta and Fas ligation. *Diabetes* 47:727-732.

27. Rabinovitch, A., Sumoski, W., Rajotte, R. V., and Warnock, G. L. 1990. Cytotoxic effects of cytokines on human pancreatic islet cells in monolayer culture. *J. Clin. Endocrinol. Metab* 71:152-156.

28. Stassi, G., De Maria, R., Trucco, G., Rudert, W., Testi, R., Galluzzo, A., Giordano, C., and Trucco, M. 1997. Nitric oxide primes pancreatic beta cells for Fas-mediated destruction in insulin-dependent diabetes mellitus. *J. Exp. Med.* 186:1193-1200.

29. Kwon, G., Corbett, J. A., Rodi, C. P., Sullivan, P., and McDaniel, M. L. 1995. Interleukin-1 beta-induced nitric oxide synthase expression by rat pancreatic beta-cells: evidence for the involvement of nuclear factor kappa B in the signaling mechanism. *Endocrinology* 136:4790-4795.

30. Darville, M. I. and Eizirik, D. L. 2001. Cytokine induction of Fas gene expression in insulin-producing cells requires the transcription factors NF-kappaB and C/EBP. *Diabetes* 50:1741-1748.

31. Flodstrom, M., Welsh, N., and Eizirik, D. L. 1996. Cytokines activate the nuclear factor kappa B (NF-kappa B) and induce nitric oxide production in human pancreatic islets. *FEBS Lett* 385:4-6.

32. Linetsky, E., Bottino, R., Lehmann, R., Alejandro, R., Inverardi, L., and Ricordi, C. 1997. Improved human islet isolation using a new enzyme blend, liberase. *Diabetes* 46:1120-1123.

33. Oberholzer, J., Triponez, F., Mage, R., Andereggen, E., Buhler, L., Cretin, N., Fournier, B., Goumaz, C., Lou, J., Philippe, J. et al. 2000. Human islet transplantation: lessons from 13 autologous and 13 allogeneic transplantations. *Transplantation* 69:1115-1123.

34. Ricordi, C., Lacy, P. E., Finke, E. H., Olack, B. I., and Scharp, D. W. 1988. Automated method for isolation of human pancreatic islets. *Diabetes* 37:413-420.

35. Kaiser, N., Corcos, A. P., Sarel, I., and Cerasi, E. 1991. Monolayer culture of adult rat pancreatic islets on extracellular matrix: modulation of β-cell function by chronic exposure to high glucose. *Endocrinology* 129:2067-2076.

36. Jodo, S., Xiao, S., Hohlbaum, A., Strehlow, D., arshak-Rothstein, A., and u, S. T. 2001. Apoptosis-inducing membrane vesicles. A novel agent with unique properties. *J Biol Chem* 276:39938-39944.

37. Schneemann, M., Schoedon, G., Hofer, S., Blau, N., Guerrero, L., and Schaffner, A. 1993. Nitric oxide synthase is not a constituent of the antimicrobial armature of human mononuclear phagocytes. *J Infect Dis* 167:1358-1363.

38. Gavrieli, Y., Sherman, Y., and Ben-Sasson, S. A. 1992. Identification of programmed cell death in situ via specific labeling of nuclear DNA fragmentation. *J Cell Biol* 119: 493-501.

39. Toledano, M. B., Ghosh, D., Trinh, F., and Leonard, W. J. 1993. N-terminal DNA-binding domains contribute to differential DNA-binding specificities of NF-kappa B p50 and p65. *Mol Cell Biol* 13:852-860.

40. Karin, M. 1999. How NF-kappaB is activated: the role of the IkappaB kinase (IKK) complex. *Oncogene* 18:6867-6874.

41. Mathis, D., Vence, L., and Benoist, C. 2001. beta-Cell death during progression to diabetes. *Nature* 414:792-798.

42. Pietropaolo, M., Barinas-Mitchell, E., Pietropaolo, S. L., Kuller, L. H., and Trucco, M. 2000. Evidence of islet cell autoimmunity in elderly patients with type 2 diabetes. *Diabetes* 49:32-38.

43. Rowley, M. J., Mackay, I. R., Chen, Q. Y., Knowles, W. J., and Zimmet, P. Z. 1992. Antibodies to glutamic acid decarboxylase discriminate major types of diabetes mellitus. *Diabetes* 41:548-551.

44. Wilkin, T. J. 2001. The accelerator hypothesis: weight gain as the missing link between Type I and Type II diabetes. *Diabetologia* 44:914-922.

45. Bellone, M., Iezzi, G., Rovere, P., Galati, G., Ronchetti, A., Protti, M. P., Davoust, J., Rugarli, C., and Manfredi, A. A. 1997. Processing of engulfed apoptotic bodies yields T cell epitopes. *J. Immunol.* 159:5391-5399.

46. Trudeau, J. D., Dutz, J. P., Arany, E., Hill, D. J., Fieldus, W. E., and Finegood, D. T. 2000. Neonatal beta-cell apoptosis: a trigger for autoimmune diabetes? *Diabetes* 49:1-7.

47. Lacy, P. E. and Finke, E. H. 1991. Activation of intraislet lymphoid cells causes destruction of islet cells. *Am. J. Pathol.* 138:1183-1190.

48. Lacy, P. E. 1994. The intraislet macrophage and type I diabetes. *Mt. Sinai J. Med.* 61:170-174.

49. Arnush, M., Scarim, A. L., Heitmeier, M. R., Kelly, C. B., and Corbett, J. A. 1998. Potential role of resident islet macrophage activation in the initiation of autoimmune diabetes. *J Immunol* 160:2684-2691.

50. Heitmeier, M. R., Arnush, M., Scarim, A. L., and Corbett, J. A. 2001. Pancreatic {beta}-cell damage mediated by {beta}-cell production of IL-1: A novel mechanism for virus-induced diabetes. *J Biol Chem* 276:11151-11158.

51. Gadot, M., Leibowitz, G., Shafrir, E., Cerasi, E., Gross, D. J., and Kaiser, N. 1994. Hyperproinsulinemia and insulin deficiency in the diabetic *Psammomys obesus*. *Endocrinology* 135:610-616.

52. Chen, M. C., Proost, P., Gysemans, C., Mathieu, C., and Eizirik, D. L. 2001.—Monocyte chemoattractant protein-1 is expressed in pancreatic islets from prediabetic NOD mice and in interleukin-1 beta-exposed human and rat islet cells. *Diabetologia* 44:325-332.

53. Eizirik, D. L. and Darville, M. I. 2001. beta-cell apoptosis and defense mechanisms: lessons from type 1 diabetes. *Diabetes* 50:S64-S69.

54. Liu, D., Pavlovic, D., Chen M C, Flodstrom, M., Sandler, S., and Eizirik, D. L. 2000. Cytokines induce apoptosis in beta-cells isolated from mice lacking the inducible isoform of nitric oxide synthase (iNOS−/−). *Diabetes* 49:1116-1122.

55. Zumsteg, U., Frigerio, S., and Hollander, G. A. 2000. Nitric oxide production and Fas surface expression mediate two independent pathways of cytokine-induced murine beta-cell damage. *Diabetes* 49:39-47.

56. Giannoukakis, N., Rudert, W. A., Trucco, M., and Robbins, P. D. 2000. Protection of human islets from the effects of interleukin-1beta by adenoviral gene transfer of an Ikappa B repressor. *J Biol Chem* 275:36509-36513.

57. Corbett, J. A., Sweetland, M. A., Wang, J. L., Lancaster, J. R., Jr., and McDaniel, M. L. 1993. Nitric oxide mediates cytokine-induced inhibition of insulin secretion by human islets of Langerhans. *Proc. Natl. Acad. Sci. U.S.A* 90:1731-1735.

58. Yerneni K. K., Bai, W., Khan B. V., Medford R. M., and Natarajan, R. 1999. Hyperglycemia-induced activation of nuclear transcription factor kappaB in vascular smooth muscle cells. *Diabetes* 48:855-864.

59. Heimberg, H., Heremans, Y., Jobin, C., Leemans, R., Cardozo, A. K., Darville, M., and Eizirik, D. L. 2001. Inhibition of cytokine-induced NF-kappaB activation by adenovirus-mediated expression of a NF-kappaB super-repressor prevents beta-cell apoptosis. *Diabetes* 50:2219-2224.

60. Zaitsev, S. V., Appelskog, I. B., Kapelioukh, I. L., Yang, S.-N., Kohler, M., Efendic, S. and Berggren, P.-O. 2001. Imidazoline Compounds Protect Against Interleukin 1β-Induced β-Cell Apoptosis. *Diabetes* 50, Supp. 1: S70-S76.

61. Glaser, B, Leibovich, G, Nesher, R, Hartling, S, Binder, C, Cerasi, E: Improved beta-cell function after intensive insulin treatment in severe non-insulin-dependent diabetes. Acta Endocrinol. (Copenh) 118:365-373, 1988.

62. Butler, A E, Janson, J, Bonner-Weir, S, Ritzel, R, Rizza, R A, Butler, P C: Beta-Cell deficit and increased Beta-Cell Apoptosis in humans with Type-2 Diabetes Mellitus. Diabetes 52:102-110, 2003.

63. Jensen, C. B., Storgaard, H., Dela, F., Holst, J. J., Madsbad, S., and Vaag, A. A. Early differential defects of insulin secretion and action in 19-year-old caucasian men who had low birth weight. Diabetes 51:1271-1280, 2002

64. Poulsen, P., Levin, K., Beck-Nielsen, H., and Vaag, A. Age-dependent impact of zygosity and birth weight on insulin secretion and insulin action in twins. Diabetologia 45:1649-1657, 2002.

65. Vaag, A., Lehtovirta, M., Thye-Ronn, P., and Groop, L. Metabolic impact of a family history of Type 2 diabetes. Results from a European multicentre study (EGIR). Diabet. Med. 18:533-540, 2001.

66. Bonner-Weir, S. 2000. Islet growth and development in the adult. *J. Mol. Endocrinol.* 24:297-302.

67. Kloppel, G., Lohr, M., Habich, K., Oberholzer, M., and Heitz, P. U. 1985. Islet pathology and the pathogenesis of type 1 and type 2 diabetes mellitus revisited. *Surv Synth Pathol Res* 4:110-125.

68. Sakuraba, H., Mizukami, H., Yagihashi, N., Wada, R., Hanyu, C., and Yagihashi, S. 2002. Reduced beta-cell mass and expression of oxidative stress-related DNA damage in the islet of Japanese Type II diabetic patients. *Diabetologia* 45:85-96.

69. Yoon, K. H., Ko, S. H., Cho, J. H., Lee, J. M., Ahn, Y. B., Song, K. H., Yoo, S. J., Kang, M. I., Cha, B. Y., Lee, K. W. et al. 2003. Selective beta-Cell Loss and alpha-Cell Expansion in Patients with Type 2 Diabetes Mellitus in Korea. *J. Clin. Endocrinol. Metab* 88:2300-2308.

70. Donath, M. Y., Gross, D. J., Cerasi, E., and Kaiser, N. 1999. Hyperglycemia-induced beta-cell apoptosis in pancreatic islets of *Psammomys obesus* during development of diabetes. *Diabetes* 48:738-744.

71. LeRoith, D. 2002. Beta-cell dysfunction and insulin resistance in type 2 diabetes: role of metabolic and genetic abnormalities. *Am. J. Med.* 113 Suppl 6A:3S-115.

72. McGarry, J. D. and Dobbins, R. L. 1999. Fatty acids, lipotoxicity and insulin secretion. *Diabetologia* 42:128-138.

73. Randle, P. J., Garland, P. B., Newsholme, E. A., and Hales, C. N. 1965. The glucose fatty acid cycle in obesity and maturity onset diabetes mellitus. *Ann. N.Y. Acad. Sci.* 131:324-333.

74. Unger, R. H. 1995. Lipotoxicity in the pathogenesis of obesity-dependent NIDDM. Genetic and clinical implications. *Diabetes* 44:863-870.

75. Maedler, K., Oberholzer, J., Bucher, P., Spinas, G. A., and Donath, M. Y. 2003. Monounsaturated Fatty Acids Prevent the Deleterious Effects of Palmitate and High Glucose on Human Pancreatic beta-Cell Turnover and Function. *Diabetes* 52:726-733.

76. Maedler, K., Sergeev, P., Ris, F., Oberholzer, J., Joller-Jemelka, H. I., Spinas, G. A., Kaiser, N., Halban, P. A., and Donath, M. Y. 2002. Glucose-induced beta-cell production of interleukin-1beta contributes to glucotoxicity in human pancreatic islets. *J. Clin. Invest* 110:851-860.

77. Maedler, K., Fontana, A., Ris, F., Sergeev, P., Toso, C., Oberholzer, J., Lehmann, R., Bachmann, F., Tasinato, A., Spinas, G. A. et al. 2002. FLIP switches Fas-mediated glucose signaling in human pancreatic β cells from apoptosis to cell replication. *Proc. Natl. Acad. Sci. U.S.A* 99:8236-8241.

78. Weir, G. C., Clore, E. T., Zmachinski, C. J., and Bonner-Weir, S. 1981. Islet secretion in a new experimental model for non-insulin-dependent diabetes. *Diabetes* 30:590-595.

79. Bonner-Weir, S., Trent, D. F., and Weir, G. C. 1983. Partial pancreatectomy in the rat and subsequent defect in glucose-induced insulin release. J. Clin. Invest 71:1544-1553.

80. Unger, R. H. and Grundy, S. 1985. Hyperglycaemia as an inducer as well as a consequence of impaired islet cell function and insulin resistance: implications for the management of diabetes. *Diabetologia* 28:119-121.

81. Zhang, Y., Proenca, R., Maffel, M., Barone, M., Leopold, L., and Friedman, J. M. 1994. Positional cloning of the mouse obese gene and its human homologue. *Nature* 372:425-432.

82. Campfield, L. A., Smith, F. J., Guisez, Y., Devos, R., and Burn, P. 1995. Recombinant mouse OB protein: evidence for a peripheral signal linking adiposity and central neural networks. *Science* 269:546-549.

83. Emilsson, V., Liu, Y. L., Cawthorne, M. A., Morton, N. M., and Davenport, M. 1997. Expression of the functional leptin receptor mRNA in pancreatic islets and direct inhibitory action of leptin on insulin secretion. *Diabetes* 46:313-316.

84. Kieffer, T. J., Heller, R. S., and Habener, J. F. 1996. Leptin receptors expressed on pancreatic beta-cells. *Biochem. Biophys. Res. Commun.* 224:522-527.

85. Roduit, R. and Thorens, B. 1997. Inhibition of glucose-induced insulin secretion by long-term preexposure of pancreatic islets to leptin. *FEBS Lett.* 415:179-182.

86. Islam, M. S., Sjoholm, A., and Emilsson, V. 2000. Fetal pancreatic islets express functional leptin receptors and leptin stimulates proliferation of fetal islet cells. *Int. J. Obes. Relat Metab Disord.* 24:1246-1253.

87. Okuya, S., Tanabe, K., Tanizawa, Y., and Oka, Y. 2001. Leptin increases the viability of isolated rat pancreatic islets by suppressing apoptosis. *Endocrinology* 142:4827-4830.

88. Shimabukuro, M., Wang, M. Y., Zhou, Y. T., Newgard, C. B., and Unger, R. H. 1998. Protection against lipoapoptosis of beta cells through leptin-dependent maintenance of Bcl-2 expression. *Proc Natl Acad Sci USA* 95:9558-9561.

89. Tanabe, K., Okuya, S., Tanizawa, Y., Matsutani, A., and Oka, Y. 1997. Leptin induces proliferation of pancreatic beta cell line MIN6 through activation of mitogen-activated protein kinase. *Biochem. Biophys. Res. Commun.* 241:765-768.
90. Seckinger, P., Williamson, K., Balavoine, J. F., Mach, B., Mazzei, G., Shaw, A., and Dayer, J. M. 1987. A urine inhibitor of interleukin 1 activity affects both interleukin 1 alpha and 1 beta but not tumor necrosis factor alpha. *J. Immunol.* 139:1541-1545.
91. Seckinger, P., Lowenthal, J. W., Williamson, K., Dayer, J. M., and MacDonald, H. R. 1987. A urine inhibitor of interleukin 1 activity that blocks ligand binding. *J. Immunol.* 139:1546-1549.
92. Arend, W. P. and Guthridge, C. I. 2000. Biological role of interleukin 1 receptor antagonist isoforms. *Ann. Rheum. Dis.* 59 Suppl 1:i60-i64.
93. Gabay, C., Dreyer, M., Pellegrinelli, N., Chicheportiche, R., and Meier, C. A. 2001. Leptin directly induces the secretion of interleukin 1 receptor antagonist in human monocytes. *J. Clin. Endocrinol. Metab* 86:783-791.
94. Donath, M. Y., Storling, J., Maedler, K., and Mandrup-Poulsen, T. Inflammatory mediators and islet beta-cell failure: a link between Type 1 and Type 2 diabetes. *J Mol Med, In Press.* 2003.
95. Polonsky, K. S., Sturis, J., and Bell, G. I. 1998. Seminars in Medicine of the Beth Israel Hospital, Boston. Non-insulin-dependent diabetes mellitus—a genetically programmed failure of the beta cell to compensate for insulin resistance. *N Engl J Med* 334:777-783.

The invention claimed is:

1. A method of treating type 2 diabetes or prophylactically suppressing type 2 diabetes in a mammal predisposed to type 2 diabetes, the method comprising administering to a mammal in need thereof a medicament comprising a sufficient amount of anakinra.

2. The method according to claim 1, wherein the medicament is adapted for parenteral administration.

3. The method according to claim 2, wherein anakinra is administered to the mammal in a dose of 0.1 to 1000 mg of anakinra per kg of body weight.

4. The method according to claim 1, wherein the medicament further comprises pyrrolidinedithiocarbamate (PDTC).

5. The method according to claim 4, wherein the medicament is adapted for parenteral administration.

6. The method according to claim 5, wherein the anakinra is administered to the mammal in a dose of 0.1 to 1000 mg of anakinra per kg of body weight.

7. The method according to claim 6, wherein the PDTC is administered to the mammal in a dose of 0.1 to 1000 mg of PDTC per kg of body weight.

8. A method of treating type 2 diabetes, the method comprising administering to a mammal in need thereof a dose of 0.1 to 1000 mg of anakinra per kg of body weight.

9. The method according to claim 8, wherein the medicament is administered via parenteral administration.

10. The method according to claim 8, wherein the medicament further comprises pyrrolidinedithiocarbamate (PDTC).

11. The method according to claim 10, wherein the medicament is administered by parenteral administration.

12. The method according to claim 11, wherein the PDTC is administered to the mammal in a dose of 0.1 to 1000 mg of PDTC per kg of body weight.

* * * * *

UNITED STATES PATENT AND TRADEMARK OFFICE
CERTIFICATE OF CORRECTION

| | | |
|---|---|---|
| PATENT NO. | : 7,572,770 B2 | Page 1 of 1 |
| APPLICATION NO. | : 10/517450 | |
| DATED | : August 11, 2009 | |
| INVENTOR(S) | : Donath | |

It is certified that error appears in the above-identified patent and that said Letters Patent is hereby corrected as shown below:

On the title page,

[*] Notice:   Subject to any disclaimer, the term of this patent is extended or adjusted under 35 USC 154(b) by (219) days Delete the phrase "by 219 days" and insert -- by 573 days --

Signed and Sealed this

Sixth Day of April, 2010

David J. Kappos
*Director of the United States Patent and Trademark Office*

SEQUENCE LISTING

```
<160> NUMBER OF SEQ ID NOS: 8

<210> SEQ ID NO 1
<211> LENGTH: 20
<212> TYPE: DNA
<213> ORGANISM: Homo sapiens

<400> SEQUENCE: 1
actgaggacc agccattgag                                              20

<210> SEQ ID NO 2
<211> LENGTH: 20
<212> TYPE: DNA
<213> ORGANISM: Homo sapiens

<400> SEQUENCE: 2
aggtggaatg agggaggaag                                              20

<210> SEQ ID NO 3
<211> LENGTH: 20
<212> TYPE: DNA
<213> ORGANISM: Homo sapiens

<400> SEQUENCE: 3
aagctgatgg ccctaaacag                                              20

<210> SEQ ID NO 4
<211> LENGTH: 20
<212> TYPE: DNA
<213> ORGANISM: Homo sapiens

<400> SEQUENCE: 4
aggtgcatcg tgcacataag                                              20

<210> SEQ ID NO 5
<211> LENGTH: 20
<212> TYPE: DNA
<213> ORGANISM: Homo sapiens

<400> SEQUENCE: 5
agagtcgcgc tgtaagaagc                                              20

<210> SEQ ID NO 6
<211> LENGTH: 20
<212> TYPE: DNA
<213> ORGANISM: Homo sapiens
```

```
<400> SEQUENCE: 6
tggtcttgtc acttggcatc                                               20

<210> SEQ ID NO 7
<211> LENGTH: 20
<212> TYPE: DNA
<213> ORGANISM: Homo sapiens

<400> SEQUENCE: 7
aacagcgaca cccactcctc                                               20

<210> SEQ ID NO 8
<211> LENGTH: 21
<212> TYPE: DNA
<213> ORGANISM: Homo sapiens

<400> SEQUENCE: 8 ggagggggaga ttcagtgtgg t                                            21
```